United States Patent [19]
Wain-Hobson et al.

[11] Patent Number: 5,843,730
[45] Date of Patent: Dec. 1, 1998

[54] METHOD FOR HYPERMUTAGENESIS OF NUCLEOTIDES

[75] Inventors: Simon Wain-Hobson, Montiguy le Bretonneloc, France; Miguel Angel Martinez, Madrid, Spain; Valérie Pezo, Paris, France

[73] Assignee: Institut Pasteur, Paris, France

[21] Appl. No.: 447,173

[22] Filed: May 19, 1995

[30] Foreign Application Priority Data

Dec. 2, 1994 [EP] European Pat. Off. ............... 94402774

[51] Int. Cl.[6] .................................................. C12P 19/34
[52] U.S. Cl. .................... 435/91.1; 435/91.2; 435/91.21; 435/91.3; 435/91.51; 435/69.1
[58] Field of Search ............................. 435/6, 91.1, 91.2, 435/69.1, 320.1, 91.21, 9.13, 91.51, 91.4, 91.41

[56] References Cited

FOREIGN PATENT DOCUMENTS 0 285 123 A2  10/1988  European Pat. Off. ........ C12N 15/00

OTHER PUBLICATIONS

Miguel Angel Martinez et al., "Hypermutagenesis of RNA using human immunodeficiency virus type 1 reverse transcriptase and biased dNTP concentrations", Proc. Natl. Acad. Sci., vol. 91, No. 25, Dec. 6, 1994, pp. 11781–11791.

Jean–Pierre Vartanian et al., G→A hypermutation of the human inmmunodeficency virus type 1 genome: Evidence for dCTP pool imbalance during reverse transcription, Proc. Natl. Acad. Sci. vol. 91, No. 8, Apr. 12, 1994, pp. 3092–3096.

P. M. Lehtovaara et al., "A new method for randam mutagenesis of complete genes: enzymatic generation of mutant libraries in vitro", Protein Engineering, vol. 2, No. 1, Apr. 1988, pp. 63–68.

Philip Piura, et al., "Development of an in vitro method to identify mutants of phage T4 lysozome of enhanced thermostability", Protein Science, vol. 2, No. 12, Dec. 1993, pp. 2217–2225.

Roberto Cattaneo et al., "Biased Hypermutation and Other Genetic Changes In Defective Measles Viruses in Human Brain Infections", Cell, vol. 55, No. 2 Oct. 21, 1988, pp. 255–265.

S. Kwok et al., "Effects of primer–template mismatches on the polymerase chain reaction: Human immunodeficiency virus type 1 model studies", Nucleic Acid Research, vol. 18, No. 4, Feb. 25, 1990, pp. 999–1005.

Ralf Sommer et al., "Minimal homology requirements for PCR primers", Nucleic Acid Research, vol. 17, No. 16, Aug. 25, 1990, p. 6749.

Gerald F. Joyce, "Amplification, mutation and selection of catalytic RNA", Gene, vol. 82, No, 1, Oct. 1989, pp. 83–87.

Jean–Pierre Vartanian et al., "Selection, Recombination, and G→A Hypermutation of Human Immunodeficiency Virus Type 1 Genomes", J. Virol., vol. 65, No. 4, Apr. 1994, pp. 1779–1788.

Fromant et al. (1995) Anal. Biochem. 224:347–53.

Ueda et al. (1995) J. Fermentation and Bioengineering 79:303–5.

Leung et al. (1989) Technique 1:11–15.

Liao and Wise (1990) Gene 88:107–111.

*Primary Examiner*—W. Gary Jones
*Assistant Examiner*—Amy Atzel
*Attorney, Agent, or Firm*—Finnegan, Henderson, Farabow, Garrett & Dunner, L.L.P.

[57] ABSTRACT

The present invention features a method for introducing hypermutations into a target DNA or RNA sequence of interest, characterized in that said method comprises the steps of:

(a) transcribing a RNA into DNA in a reaction mixture comprising a reverse transcriptase, varying biased concentrations of deoxynucleoside triphosphates to produce hypermutations and an oligonucleotide primer that is partially complementary to the 3' end of said RNA; and (b) recovering said DNA sequences.

45 Claims, 10 Drawing Sheets

5' CGG GAGCTC CACACAAAGGAACCAAATG        forward primer
    clamp  SacI    R67 specific 5' CCG GGATCC AACACCCAACCACCAACTTA        backward primer
    clamp  BamHI  R67 specific

FIG. 4 forward primer
5' GCACCG GAGCTC ATTAACCCTCACTAAAGGGA CACACAAAGGAACCAAATG        R67 specific
    clamp  SacI   T3 promoter backward primer
5' GCACCG GGATCC AATTTAATACGACTCACTATAGGG AACACCCAACCACCAACTTA    R67 specific
    clamp  BamHI  T7 promoter

```
     SacI                      Met Glu Arg Ser Ser Asn Glu Val Ser Asn Pro Val Ala Gly
5'  GAGCTC CACAACAAAGGAACCAA    ATG GAA CGA AGT AGC AAT GAA GTC AGT AAT CCA GTT GCT GGC

Asn Phe Val Phe Pro Ser Asn Ala Thr Phe Val Met Gly Asp Arg Val Arg Lys Lys Ser
    AAT TTT GTA TTC CCA TCG AAC GCC ACG TTT ATG GGA GAT CGC GTG CGC AAG AAA TCC

Gly Ala Ala Trp Gln Gly Gln Ile Val Gly Trp Tyr Cys Thr Asn Leu Thr Pro Glu Gly
    GGC GCC GCC TGG CAA GGT CAA ATT GTC GGG TGG TAC TGC ACA AAT TTG ACC CCC GAA GGC

Tyr Ala Val Glu Ser Glu Ala His Pro Gly Ser Val Gln Ile Tyr Pro Val Ala Ala Leu
    TAC GCC GTC GAG TCT GAG GCT CAC CCA GGC TCA GTA CAG ATT TAT CCT GTT GCG GCG CTT

Glu Arg Ile Asn Stop                          BamHI
    GAA CGC ATC AAC TAA TAAGTTGGTGGTTGGGTGTT GGATCC
```

FIG. 5

```
primer 4
       GAGCTC CACAACAAGGAACCAA ATG →
                              Met Glu Arg Ser Ser Asn Glu Val Ser Asn Pro Val Ala Gly
5'     GAGCUC CACAACAAGGAACCAA AUG GAA CGA AGU AGC AAU GAA GUC AGU AAU CCA GUU GCU GGC Asn Phe Val Phe Pro Ser Asn Ala Thr Phe Gly Met Gly Asp Arg Val Arg Lys Lys Ser
AAU UUU GUA UUC CCA UCG AAC GCC ACG UUU GGU AUG GGA GAU CGC GUG CGC AAG AAA UCC
                                              ↓ C CCT CTA GCG CAC GCG primer 1

Gly Ala Ala Trp Gln Gly Gln Ile Val Gly Trp Tyr Cys Thr Asn Leu Thr Pro Glu Gly
GGC GCC GCC UGG CAA GGU CAA AUU GUC GGG UGG UAC UGC ACA AAU UUG ACC CCC GAA GGC
                                                                        ↓ T CCG

Tyr Ala Val Glu Ser Glu Ala His Pro Gly Ser Val Gln Ile Tyr Pro Val Ala Ala Leu
UAC GCC GUC GAG UCU GAG GCU CAC CCA GGC UCA GUA CAG AUU UAU CCU GUU GCG GCG CUU
ATG CGG CAG CTC primer 2

Glu Arg Ile Asn Stop
GAA CGC AUC AAC UAA GUUGGUGGUUGGGGUGUU GGAUCC
            ↓      ATT CAACCACCAACCCCACAA CCTAGG primer 3
```

Modified R67 gene sequence wth respect to that given in Brisson and Hohn, Gene 28, 271-275, 1984
Amino acid sequence in the three letter code given above nucleic acid sequence

SEQUENCE LISTING ( 1 ) GENERAL INFORMATION:

( i i i ) NUMBER OF SEQUENCES: 65

( 2 ) INFORMATION FOR SEQ ID NO:1:

( i ) SEQUENCE CHARACTERISTICS:
( A ) LENGTH: 55 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:1:

GCGAAGCTTA ATTTAATACG ACTCACTATA GGGACAAAGC CTAAAGCCAT GTGTA 55

( 2 ) INFORMATION FOR SEQ ID NO:2:

( i ) SEQUENCE CHARACTERISTICS:
( A ) LENGTH: 31 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:2:

GCGGAATTCT AATGTATGGG AATTGGCTCA A 31

( 2 ) INFORMATION FOR SEQ ID NO:3:

( i ) SEQUENCE CHARACTERISTICS:
( A ) LENGTH: 29 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:3:

GCGTCTAGAA GTATCATTAT CTATTGGTA 29

( 2 ) INFORMATION FOR SEQ ID NO:4:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:4:

GCGGTCGACC AAAGCCTAAA GCCA 24

( 2 ) INFORMATION FOR SEQ ID NO:5:

( i ) SEQUENCE CHARACTERISTICS:
( A ) LENGTH: 19 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:5:

TGTAAAAYYA ACCCCACYC  19

( 2 ) INFORMATION FOR SEQ ID NO:6:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

ATTAACCCTC ACTAAAGGGA  20

( 2 ) INFORMATION FOR SEQ ID NO:7:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

AATTTAATAC GACTCACTAT AGGG  24

( 2 ) INFORMATION FOR SEQ ID NO:8:

( i ) SEQUENCE CHARACTERISTICS:
        ( A ) LENGTH: 172 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:8:

AAAUUAACCC CACUCUGUGU UACUUUAAAU UGCACUGACU UAAAGAAUGC CAAUAGUAGU  60

AGCAGGGGAA UGAUGGAGAA AAGAGAAAUG AAGAACUGCU CUUUCAAUGU CACCACAAGC  120

AUAAGAAAUA AGAUGCAGAA AGAAUAUGCA CUUCUUUAUA AACUUAAUGU AG  172

( 2 ) INFORMATION FOR SEQ ID NO:9:

( i ) SEQUENCE CHARACTERISTICS:
        ( A ) LENGTH: 172 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:9:

AAAUUAACCC CACUCUGUGU UACUUUAAAU UGCACUGACU UAAAGAAUGC CAAUAAUAGU  60

AACAAGGGAA UGAUGGAGAA AAGAGAAAUG AAGAACUGCU CUUUCAAUGU CACCACAAGC  120

AUAAGAAAUA AGAUGCAGAA AGAAUAUGCA CUUCUUUAUA AACUUAAUGU AA  172

( 2 ) INFORMATION FOR SEQ ID NO:10:

( i ) SEQUENCE CHARACTERISTICS:
        ( A ) LENGTH: 172 base pairs (B) TYPE: nucleic acid
(C) STRANDEDNESS: single
(D) TOPOLOGY: linear (i i) MOLECULE TYPE: cDNA (x i) SEQUENCE DESCRIPTION: SEQ ID NO:10:

| | | | | | |
|---|---|---|---|---|---|
| AAAUUAACCC | CACUCUGUAU | UACUUUAAAU | UACACUAACU | UAAAGAAUGC | CAAUAGUAGU | 60
| AGCACGGGAA | UGAUGGAGAA | AAGAGAAAUA | AAGAACUGCU | CUUUCAAUGU | CACCACAAGC | 120
| AUAAGAAAUA | AGAUGCAGAA | AGAAUAUGCA | CUUCUUUAUA | AACUUAAUGU | AG | 172

(2) INFORMATION FOR SEQ ID NO:11:

(i) SEQUENCE CHARACTERISTICS:
(A) LENGTH: 172 base pairs
(B) TYPE: nucleic acid
(C) STRANDEDNESS: single
(D) TOPOLOGY: linear (i i) MOLECULE TYPE: cDNA (x i) SEQUENCE DESCRIPTION: SEQ ID NO:11:

| | | | | | |
|---|---|---|---|---|---|
| AAAUUAACCC | CACUCUGUAU | UACUUUAAAU | UACACUAACU | UAAAGAAUAC | CAAUAAUACU | 60
| AACAAGGAAA | UGAUGGAGAA | AAGAAGAAUG | AAGAACUACU | CUUUCAAUAU | CACCACAAGC | 120
| AUAAGAAAUA | AGAUGCAGAA | AGAAUAUGCA | CUUCUUUAUA | AACUUAAUGU | AG | 172

(2) INFORMATION FOR SEQ ID NO:12:

(i) SEQUENCE CHARACTERISTICS:
(A) LENGTH: 172 base pairs
(B) TYPE: nucleic acid
(C) STRANDEDNESS: single
(D) TOPOLOGY: linear (i i) MOLECULE TYPE: cDNA (x i) SEQUENCE DESCRIPTION: SEQ ID NO:12:

| | | | | | |
|---|---|---|---|---|---|
| AAAUUAACCC | CACUCUGUAU | UACUUUAAAU | UCCACUGACU | UAAAGAAUGC | CAAUAGUAGU | 60
| AACAGGGGAA | UGAUGGAGAA | AAGAAAAAUG | AAGAACUGCU | CUUACAAUGU | CACCACAAGC | 120
| AUAAGAAAUA | AAAUGCAAAA | AGAAUAUGCA | CUUCUUUAUA | AACUUAAUGU | AG | 172

(2) INFORMATION FOR SEQ ID NO:13:

(i) SEQUENCE CHARACTERISTICS:
(A) LENGTH: 146 base pairs
(B) TYPE: nucleic acid
(C) STRANDEDNESS: single
(D) TOPOLOGY: linear (i i) MOLECULE TYPE: cDNA (x i) SEQUENCE DESCRIPTION: SEQ ID NO:13:

| | | | | | |
|---|---|---|---|---|---|
| AAAUUACACU | GACUUAAAAA | AUACCAAUAG | UAGUAGCAAG | GGAAUGAUGG | AGAAAAGAGA | 60
| AAUGAAGAAC | UGCUCUUUCA | AUAUCACCAC | AAGCAUAAGA | AAUAAGAUGC | AGAAAGAAUA | 120
| UGCACUUCUU | UAUAAACUUA | AUAUAG | | | | 146

(2) INFORMATION FOR SEQ ID NO:14:

(i) SEQUENCE CHARACTERISTICS:
(A) LENGTH: 172 base pairs
(B) TYPE: nucleic acid
(C) STRANDEDNESS: single
(D) TOPOLOGY: linear ( i i ) MOLECULE TYPE: cDNA ( x i ) SEQUENCE DESCRIPTION: SEQ ID NO:14:

| AAAUUAACCC | CACUCUAUGU | UACUUUAAAU | UGCACUAACU | UAAAGAAUAC | CAAUAAUAGU | 60 |
| AACAAGGAAA | UGAUGGAGAA | AAGAGAAAUA | AAGAACUGCU | CUUUCAAUGU | CACCACAAGC | 120 |
| AUAAGAAAUA | AGAUGCAGAA | AGAAUAUGCA | CUUCUUUAUA | AACUUAAUGU | AG | 172 |

( 2 ) INFORMATION FOR SEQ ID NO:15:

( i ) SEQUENCE CHARACTERISTICS:
        ( A ) LENGTH: 172 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:15:

| AAAUUAACCC | CACUCUGUGU | UACUUUAAAU | UACACUGACU | UAAAAAAUGC | CAAUAAUAGU | 60 |
| AGCAAGGGAA | UGAUAGAGAA | AAGAGAAAUG | AAGAACUGCU | CUUUCAAUGU | CACCACAAAC | 120 |
| AUAAGAAAUA | AAAUGCAGAA | AGAAUAUGCA | CUUCUUUAUA | AACUUAAUGU | AG | 172 |

( 2 ) INFORMATION FOR SEQ ID NO:16:

( i ) SEQUENCE CHARACTERISTICS:
        ( A ) LENGTH: 172 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:16:

| AAAUUAACCC | CACUCUGUGU | UACUUUAAAU | UACACUAACU | UAAAAAAUGC | CAAUAAUAGU | 60 |
| AGCAGGGGAA | UGAUGGAAAA | AAGAGAAAUG | AAGAACUGCU | CUUUCAAUGU | CACCACAAGC | 120 |
| AUAAGAAAUA | AGAUGCAGAA | AGAAUAUGCA | CUUCUUUAUA | AACUUAAUGU | AG | 172 |

( 2 ) INFORMATION FOR SEQ ID NO:17:

( i ) SEQUENCE CHARACTERISTICS:
        ( A ) LENGTH: 172 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:17:

| AAAUUAACCC | CACUCUGUAU | UACUUUAAAU | UGCACUAACU | UAAAGAAUAC | CAAUAGUAGU | 60 |
| AACAGGGGAA | UGAUGAAGAA | AAGAGAAAUG | AAGAACUACU | CUUUCAAUGU | CACCACAAAC | 120 |
| AUAAGAAAUA | AAAUGCAGAA | AGAAUAUGCA | CUUCUUUAUA | AACUUAAUGU | AG | 172 |

( 2 ) INFORMATION FOR SEQ ID NO:18:

( i ) SEQUENCE CHARACTERISTICS:
        ( A ) LENGTH: 174 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:18:

| AAAUUAACCC | CACUCUGUGU | UACUUUAAAU | UGCACUGACU | UAAAGAAUGC | CAAUAGUAGU | 60 |
| AGCAGGGGAA | UGAUGGAAAA | AAAAAAGAAA | UAAAAAACUG | CUCUUUCAAU | GUCACCACAA | 120 |
| GCAUAAGAAA | UAAGAUGCAG | AAAGAAUAUG | CACUUCUUUA | UAAACUUAAU | GUAG | 174 |

(2) INFORMATION FOR SEQ ID NO:19:

(i) SEQUENCE CHARACTERISTICS:
        (A) LENGTH: 172 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:19:

| AAAUUAACCC | CACUCUAUGU | UACUUUAAAU | UACACUGACU | UAAAGAAUAC | CAAUAGUAGU | 60 |
| AGCAAGGGAA | UGAUGGAGAA | AAAAGAAAUG | AAGAACUACU | CUUUCAAUGU | CACCACAAAC | 120 |
| AUAAGAAAUA | AAAUGCAGAA | AGAAUAUGCA | CUUCUUUAUA | AACUUAAUGU | AG | 172 |

(2) INFORMATION FOR SEQ ID NO:20:

(i) SEQUENCE CHARACTERISTICS:
        (A) LENGTH: 172 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:20:

| AAAUUAACCC | CACUCUGUGU | UACUUUAAAU | UGCACUGACU | UAAAGAAUGC | CAAUAGUAGU | 60 |
| AGCAGGGGAA | UGAUGGAGAA | AAGAGAAAUA | AAGAACUGCU | CUUUCAAUGU | CACCACAAGC | 120 |
| AUAAGAAAUA | AGAUGCAGAA | AGAAUAUGCA | CUUCUUUAUA | AACUUAAUAA | AA | 172 |

(2) INFORMATION FOR SEQ ID NO:21:

(i) SEQUENCE CHARACTERISTICS:
        (A) LENGTH: 172 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:21:

| AAAUUAACCC | CACUCUGUGU | UACUUUAAAU | UGCACUGACU | UAAAGAAUGC | CAAUAGUAGU | 60 |
| AGCAGGGGAA | UGAUGGAGAA | AAGAGAAAUG | AAGAACUACU | CUUUCAAUAU | CACCACAAGC | 120 |
| AUAAGAAAUA | AGAUACAGAA | AGAAUAUACA | CUUCUUUAUA | AACUUAAUAU | AG | 172 |

(2) INFORMATION FOR SEQ ID NO:22:

(i) SEQUENCE CHARACTERISTICS:
        (A) LENGTH: 170 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:22:

| AAAUUAACCC | CACUCUAUGU | UACUUUGCAC | UGACUUAAAG | AAUGCCAAUA | GUAGUAGUAG | 60 |
| CAAGGGAAUG | AUGGAGAAAA | GAGAAAUAAA | GAACUGCUCU | UUCAAUGUCA | CCACAAGCAU | 120 |

AAGAAAUAAA AUGCAGAAAG AAUAUGCACU UCUUUAUAAA CUUAAUAUAG 170

( 2 ) INFORMATION FOR SEQ ID NO:23:

( i ) SEQUENCE CHARACTERISTICS:
        ( A ) LENGTH: 172 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:23:

AAAUUAACCC CACUCUGUGU UACUUUAAAU UGCACUGACU UAAAGAAUGC CAAUAGUAGU 60

AGCAGGGGAA UGAUGGAGAA AAGAGAAAUG AAGAACUACU CUUUCAAUAU CACCACAAAC 120

AUAAAAAAUA AGAUGCAGAA AGAAUAUACA CUUCUUUAUA AACUUAAUGU AG 172

( 2 ) INFORMATION FOR SEQ ID NO:24:

( i ) SEQUENCE CHARACTERISTICS:
        ( A ) LENGTH: 172 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:24:

AAAUUAACCC CACUCUGUGU UACCUUAAAU UGCACUGACU UAAAGAAUGC CAAUAGUAGU 60

AGCAGGGGAA UGAUGGAGAA AAGAGAAAUG AAGAACUGCU CUUUCAAUGU CACCACAAGC 120

AUAAGAAAUA AGAUGCAGAA AGAAUAUGCA CUUCUUUAUA AACUUAAUGU AG 172

( 2 ) INFORMATION FOR SEQ ID NO:25:

( i ) SEQUENCE CHARACTERISTICS:
        ( A ) LENGTH: 172 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:25:

AAAUUAACCC CACUCUGUGU UACCUUAAAC UGCACUGACU UAAAGAAUGC CAAUAGUAGU 60

AGCAGGGGAA CGAUGGAGAA AAGAGAAAUG AAGAACCGCU CUUUCAAUGU CACCACAAGC 120

ACAAGAAAUA AGAUGCAGAA AGAAUAUGCA CUUCUUUAUA AACUUAAUGU AG 172

( 2 ) INFORMATION FOR SEQ ID NO:26:

( i ) SEQUENCE CHARACTERISTICS:
        ( A ) LENGTH: 172 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:26:

AAAUUAACCC CACUCUGUGU UACUUUAAAU UGCACUGACU UAAAGAAUGC CAAUAGUAGU 60

AGCAGGGGAA UGAUGGAGAA AAGAGAAACG AAGAACUGCU CUUUCAAUGU CACCACAAGC 120

AUAAGAAAUA AGAUGCAGAA AGAAUAUGCA CUUCUUUAUA AACUUAAUGU AG 172

( 2 ) INFORMATION FOR SEQ ID NO:27:

( i ) SEQUENCE CHARACTERISTICS:
    ( A ) LENGTH: 172 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:27:

```
AAAUUAACCC CACCCUGUGU UACUUUAAAU UGCACUGACU UAAAGAAUGC CAAUAGUAGU         60
AGCAGGGGAA UGAUGGAGAA AAGAGAAAUG AAGAACUGCU CUUUCAAUGU CACCACAAGC        120
AUAAGAAAUA AGAUGCAGAA AGAAUAUGCA CCUCCUUAUA AACUUAAUGU AC                172
```

( 2 ) INFORMATION FOR SEQ ID NO:28:

( i ) SEQUENCE CHARACTERISTICS:
        ( A ) LENGTH: 172 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:28:

```
AAAUUAACCC CACUCCGUGU UACUUUAAAU UGCACUGACU UAAAGAAUGC CAAUAGUAGU         60
AGCAGGGGAA UGAUGGAGAA AAGAGAAAUG AAGAACUGCU CCUUCAAUGU CACCACAAGC        120
ACAAGAAAUA AGAUGCAGAA AGAAUAUGCA CUUCUUUAUA AACUUAAUGU AG                172
```

( 2 ) INFORMATION FOR SEQ ID NO:29:

( i ) SEQUENCE CHARACTERISTICS:
        ( A ) LENGTH: 172 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:29:

```
AAAUUAACCC CACUCUGUGU UACUUUAAAU UGCACUGACU UAAAGAAUGC CAAUAGUAGC         60
AGCAGGGGAA UGAUGGAGAA AAGAGAAAUG AAGAACUGCU CUUUCAAUGU CACCACAAGC        120
AUAAGAAAUA AGAUGCAGAA AGAAUAUGCA CUUCUUUAUA AACUUAAUGU AG                172
```

( 2 ) INFORMATION FOR SEQ ID NO:30:

( i ) SEQUENCE CHARACTERISTICS:
        ( A ) LENGTH: 172 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:30:

```
AAAUUAACCC CACUCUGUGC UACUUUAAAU UGCACUGACU UAAAGAAUGC CAAUAGUAGU         60
AGCAGGGGAA UGAUGGAGAA AAGAGAAAUG AAGAACUGCU CCUUCAAUGU CACCACAAGC        120
AUAAGAAAUA AGAUGCAGAA AGAAUAUGCA CUUCUUUAUA AACUUAAUGC AG                172
```

( 2 ) INFORMATION FOR SEQ ID NO:31:

( i ) SEQUENCE CHARACTERISTICS:
        ( A ) LENGTH: 172 base pairs
        ( B ) TYPE: nucleic acid ( C ) STRANDEDNESS: single
( D ) TOPOLOGY: linear ( i i ) MOLECULE TYPE: cDNA ( x i ) SEQUENCE DESCRIPTION: SEQ ID NO:31:

| AAAUUAACCC | CACUCUGUGU | UACUUUAAAU | UGCACUGACU | UAAAGAACGC | CAAUAGUAGU | 60 |
| AGCAGGGGAA | UGAUGGAGAA | AAGAGAAAUG | AAGAACUGCU | CUUUCAAUGU | CACCACAAGC | 120 |
| AUAAGAAAUA | AGAUGCAGAA | AGAACAUGCA | CUUCUUUAUA | AACUUAAUGU | AG | 172 |

( 2 ) INFORMATION FOR SEQ ID NO:32:

( i ) SEQUENCE CHARACTERISTICS:
        ( A ) LENGTH: 162 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:32:

| AAAUUAACCC | CACUUUAAAC | UGCACUGACU | UAAAGAAUGC | CAAUAGUAGU | AGCAGGGGAA | 60 |
| UGAUGGAGAA | AAGAGAAAUG | AAGAACUGCU | CUUUCAAUGU | CACCACAAGC | AUAAGAAAUA | 120 |
| AGAUGCAGAA | AGAAUAUGCA | CUUCUUUAUA | AACUUAAUGU | AG | | 162 |

( 2 ) INFORMATION FOR SEQ ID NO:33:

( i ) SEQUENCE CHARACTERISTICS:
        ( A ) LENGTH: 172 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:33:

| AAAUUAACCC | CACUCUGUGU | UACUUUAAAC | UGCACUGACU | UAAAGAAUGC | CAAUAAUAGU | 60 |
| AGCAGGGGAA | UGAUGGAGAA | AAGAGAAAUG | AAGAACUGCU | CUUUCAAUGU | CACCACAAGC | 120 |
| AUAAGAAAUA | AGAUGCAGAA | AGAAUAUGCA | CCUCCUUAUA | AACUUAAUGU | AG | 172 |

( 2 ) INFORMATION FOR SEQ ID NO:34:

( i ) SEQUENCE CHARACTERISTICS:
        ( A ) LENGTH: 172 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:34:

| AAAUUAACCC | CACUCUGUGU | UACCUUAAAC | UGCACUGACU | UAAAGAAUGC | CAAUAGUAGU | 60 |
| AGCAGGGGAA | UGAUGGAGAA | AAGAGAAAUG | AAGAACUGCU | CUUUCAAUGU | CACCACAAGC | 120 |
| AUAAGAAAUA | AGAUGCAGAA | AGAAUACGCA | CUUCUUUAUA | AACUUAAUGU | AG | 172 |

( 2 ) INFORMATION FOR SEQ ID NO:35:

( i ) SEQUENCE CHARACTERISTICS:
        ( A ) LENGTH: 172 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:35:

AAAUUAACCC CACUCUGUGU UACUUUAAAU UGCACUGACU UAAAGAAUGC CAAUAGUAGU 60

AGCAGGGGAA UGAUGGAGAA AAGAGAAAUG AAGAACUGCU CUUUCAAUGU CACCACAAGC 120

ACAAGAAAUA AGAUGCAGAA AGAAUAUGCA CUUCUUUAUA AACUUAAUGU AG 172

( 2 ) INFORMATION FOR SEQ ID NO:36:

( i ) SEQUENCE CHARACTERISTICS:
        ( A ) LENGTH: 172 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:36:

AAAUUAACCC CACCCCGUGU UACUUUAAAU UGCACUGACU UAAAGAAUGC CAAUAGUAGU 60

AGCAGGGGAA UGAUGGAGAC AAGAGAAAUG AAGAACUGCU CUUUCAAUGU CACCACAAGC 120

ACAAGAAAUA AGAUGCAGAA AGAAUAUGCA CUUCUUUAUA AACCUAAUGU AG 172

( 2 ) INFORMATION FOR SEQ ID NO:37:

( i ) SEQUENCE CHARACTERISTICS:
        ( A ) LENGTH: 172 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:37:

AAAUUAACCC CACUCUGUGC UACUUUAAAU UGCACUGACU UAAAGAAUGC CAAUAGUAGU 60

AGCAGGGGAA UGAUGGAGAA AAGAGAAAUG AAGAACUGCU CCUUCAAUGU CACCACAAGC 120

AUAAGAAAUA AGAUGCAGAA AGAAUAUGCA CUUCUUUAUA AACUUAAUGC AG 172

( 2 ) INFORMATION FOR SEQ ID NO:38:

( i ) SEQUENCE CHARACTERISTICS:
        ( A ) LENGTH: 172 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:38:

AAAUUAACCC CACUCUGUGU UACUUUAAAU UGCACUGACU UAAAGAAGGC CAAUAGUAGC 60

AGCAGGGGAA UGAUGGAGAA AAGAGAAAUG AAGAACUGCU CUUUCAAUGC CACCACAAGC 120

AUAAGAAAUA AGAUGCAGAA AGAAUACGCA CCUCCUUAUA AACUUAAUGU AG 172

( 2 ) INFORMATION FOR SEQ ID NO:39:

( i ) SEQUENCE CHARACTERISTICS:
        ( A ) LENGTH: 172 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:39:

AAAUUAACCC CACUCUGUAU UACUUUAAAU UGCACUGACU UAAAGAAUGC CAAUAGUAAU 60

```
AGCAGGGGAA UGAUCGAGAA AAGAGAAAUG AAGAACUGCU CUUUCAAUGU CACCACAAGC      120

AUAAGAAACA AGAUGCAGAA AGAAUAUGCA CUUCUUUAUA AACUUAAUGU AG              172
```

( 2 ) INFORMATION FOR SEQ ID NO:40:

( i ) SEQUENCE CHARACTERISTICS:
        ( A ) LENGTH: 172 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:40:

```
AAAUUAACCC CACUCUGUGU UACUUUAAAU UGCACUGACU UAAAGAAUGC CAAUAGUAGU      60

AGCAGGGGAA CGAUCGAGAA AAGAAAAAUG AAGAACUGCU CUUUCAAUGU CACCACAAGC     120

AUAAGAAAUA AGAUGCAGAA AGAAUAUGCA CUUCUUUAUA AACUUAAUGU AA             172
```

( 2 ) INFORMATION FOR SEQ ID NO:41:

( i ) SEQUENCE CHARACTERISTICS:
        ( A ) LENGTH: 172 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:41:

```
AAAUUAACCC CACCCUGUGU UACUUUAAAU UGCACUGACU UAAAGAAUGC CAAUAAUAGU      60

AGCAGGGGAA UGAUGGAGAA AAGAGAAAUG AAGAACUGCU CUUUCAAUGU CACCACAAGC     120

ACAAGAAAUA AGAUGCAGAA AGAAUAUGCA CUUCUUUAUA AACUUAAUGU AG             172
```

( 2 ) INFORMATION FOR SEQ ID NO:42:

( i ) SEQUENCE CHARACTERISTICS:
        ( A ) LENGTH: 172 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:42:

```
AAAUUAACCC CACCCUGUGU UACUUUAAAU UGCACUGACU UAAAGAAUGC CAAUAGUAAU      60

AGCAGGGGAA UGAUCGAGAA AAGAGAAAUG AAGAACUGCU CUUUCAAUGU CACCACAAGC     120

AUAAGAAAUA AAAUGCAGAA AGAAUAUGCA CUUCUUUAUA AACUUAAUGU AG             172
```

( 2 ) INFORMATION FOR SEQ ID NO:43:

( i ) SEQUENCE CHARACTERISTICS:
        ( A ) LENGTH: 172 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:43:

```
AAACUAACCC CACUCUGUGU UACUUUAAAU UGCACUGACU UAAAGAAUGC CAAUAGUAGU      60

AGCAGGGGAA UAAUCGAGAA AAGAGAAAUG AAGAACUGCU CUUUCAAUAU CACCACAAAC     120

AUAAGAAAUA AGAUGCAGAA AGAAUAUGCA CUUCUUUAUA AACUUAAUGU AG             172
```

( 2 ) INFORMATION FOR SEQ ID NO:44:

( i ) SEQUENCE CHARACTERISTICS:
        ( A ) LENGTH: 165 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:44:

```
AAACUAACCC CACUCAUUAC CUUAAAUUGC ACUGACUUAA AUGCCAAUAG UAGUAGCAGG        60
GAAUGAUCGA GAAAAGAGAA AUGAAGAACU GCUCUUUCAA UGUCACCACA AGCAUAAGAA       120
ACAAGAUGCA GAAAGAAUAU GCACUUCUUU AUAAACUUAA UGUAG                      165
```

( 2 ) INFORMATION FOR SEQ ID NO:45:

( i ) SEQUENCE CHARACTERISTICS:
        ( A ) LENGTH: 172 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:45:

```
AAAUUAACCC CACUCUGUGU UACACUAAAU UGCACUGACU UAAAGAAUGC CAAUAGUAGU        60
AGCAGGGGAA CGAUCGAGAA AAGAGAAAUG AAGAACUGCU CUUUCAAUGU CACCACAAGC       120
AUAAGAAAUA AGAUGCAGAA AGAAUAUGCA CCUCCUUAUA AACUUAAUGU AG               172
```

( 2 ) INFORMATION FOR SEQ ID NO:46:

( i ) SEQUENCE CHARACTERISTICS:
        ( A ) LENGTH: 172 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:46:

```
AAAUUAACCC CACCCCGUGU UACUUUAAAU UGCACUGACU UAAAGAAUGC CAAUAGUAGU        60
AGCAGAGGAA UGAUGGAGAA AAGAGAAAUG AAGAACUGCU CUUUCAAUGU CACCACAAGC       120
AUAAGAAAUA AGAUGCAGAA AGAAUAUGCA CUUCUUUAUA AACUUAAUGU AG               172
```

( 2 ) INFORMATION FOR SEQ ID NO:47:

( i ) SEQUENCE CHARACTERISTICS:
        ( A ) LENGTH: 162 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:47:

```
AAAUUAACCC CACACUAAAU UGCACUGACU UAAAGAAUGC CAAUAGUAGC AGCAGGGGAA        60
UGAUGAAGAA AAGAGAAAUG AAGAACUGCU CUUUCAAUGU CACCACAAGC AUAAGAAAUA       120
AGAUGCAGAA AGAAUAUGCA CUUCUUUAUA AACUUAAUGU AG                         162
```

( 2 ) INFORMATION FOR SEQ ID NO:48:

( i ) SEQUENCE CHARACTERISTICS:
   ( A ) LENGTH: 172 base pairs
   ( B ) TYPE: nucleic acid
   ( C ) STRANDEDNESS: single
   ( D ) TOPOLOGY: linear ( i i ) MOLECULE TYPE: cDNA ( x i ) SEQUENCE DESCRIPTION: SEQ ID NO:48:

| AAAUUACCC | CACUCUGUGU | UACCUUAAAU | UGCACUGACU | UAAAGAAUGC | CAAUAGUAGU | 60 |
| AGCAGGGGAA | UGAUCGAGAA | AAGAGAAAUG | AAGAACUGCU | CUUCCAAUGU | CACCACAAAC | 120 |
| AUAAGAAAUA | AGAUGCAGAA | AGAAUAUGCA | CUUCUUUAUA | AACUUAAUGU | AG | 172 |

( 2 ) INFORMATION FOR SEQ ID NO:49:

( i ) SEQUENCE CHARACTERISTICS:
   ( A ) LENGTH: 172 base pairs
   ( B ) TYPE: nucleic acid
   ( C ) STRANDEDNESS: single
   ( D ) TOPOLOGY: linear ( i i ) MOLECULE TYPE: cDNA ( x i ) SEQUENCE DESCRIPTION: SEQ ID NO:49:

| AAAUUACCC | CACUCUGUGU | UACUUAAAU | UACACUGACU | UAAAGAAUGC | CAAUAGUAGU | 60 |
| AGCAGGGGAA | UGAUCGAGAA | AAGAGAAAUG | AAGAACUGCU | CCUUCAAUGU | CACCACAAAC | 120 |
| AUAAGAAAUA | AGAUGCAGAA | AGAAUAUGCA | CUUCUUUAUA | AACUUAAUGU | AG | 172 |

( 2 ) INFORMATION FOR SEQ ID NO:50:

( i ) SEQUENCE CHARACTERISTICS:
   ( A ) LENGTH: 172 base pairs
   ( B ) TYPE: nucleic acid
   ( C ) STRANDEDNESS: single
   ( D ) TOPOLOGY: linear ( i i ) MOLECULE TYPE: cDNA ( x i ) SEQUENCE DESCRIPTION: SEQ ID NO:50:

| AAAUUACCC | CACUCUGUGU | UACUUUAAAU | UGCACUGACU | UAAAGAAUGC | CAAUAAUAGU | 60 |
| AGCAGGGGAA | UGAUCGAGAA | AAGAGAAAUG | AAGAACUGCU | CUUUCAAUGU | CACCACAAAC | 120 |
| AUAAGAAACA | AGAUGCAGAA | AGAAUAUGCA | CUUCUUUAUA | AACUUAAUGU | AG | 172 |

( 2 ) INFORMATION FOR SEQ ID NO:51:

( i ) SEQUENCE CHARACTERISTICS:
   ( A ) LENGTH: 171 base pairs
   ( B ) TYPE: nucleic acid
   ( C ) STRANDEDNESS: single
   ( D ) TOPOLOGY: linear ( i i ) MOLECULE TYPE: cDNA ( x i ) SEQUENCE DESCRIPTION: SEQ ID NO:51:

| AAAUUACCC | CACUCUGUGU | UACUUAAAAU | GCACUAACUU | AAAGAAUGCC | AAUAGUAGUA | 60 |
| ACAGGGGAAU | GAUCGAGAAA | AGAAAAAUGA | AGAACUGCUC | UUCAAUGUCA | CCACAAGCAU | 120 |
| AAGAAAAUAA | GAUGCAAAAA | GAAUAUGCAC | UUCUUUAUAA | ACUUAAUGUA | G | 171 |

( 2 ) INFORMATION FOR SEQ ID NO:52:

( i ) SEQUENCE CHARACTERISTICS:
   ( A ) LENGTH: 172 base pairs
   ( B ) TYPE: nucleic acid
   ( C ) STRANDEDNESS: single ( D ) TOPOLOGY: linear ( i i ) MOLECULE TYPE: cDNA ( x i ) SEQUENCE DESCRIPTION: SEQ ID NO:52:

AAAUUAACCC CACUCUGUGU UACCUUAAAU UGCACCGACU UAAAGAAUGC CAAUAGUAGU    60

AGCAGGGGAA UGAUCGAGAA AAGAGAAAUG AAGAACUGCU CUUUCAAUGU CACCACAAGC   120

AUAAGAAAUA AGAUGCAGAA AGAAUAUGCA CUUCUUUAUA AACUUAAUGU AG           172

( 2 ) INFORMATION FOR SEQ ID NO:53:

( i ) SEQUENCE CHARACTERISTICS:
        ( A ) LENGTH: 168 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:53:

AAAUUAACCC CACUCUGUAU UACUUUAAAU UGCACUGACU UAAAGAAUGC CAAUCGUAGU    60

AGCAGGGGAA UGAUCGAGAA AAGAUGAAGA ACUGCUCUUU CAAUGUCACC ACAAGCAUAA   120

GAAAUAAGAU GCAGAAAGAA UAUGCACUUC UUUAUAAACU UAAUGUAA                168

( 2 ) INFORMATION FOR SEQ ID NO:54:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:54:

CGGGAGCTCC ACAACAAAGG AACCAAATG                                     29

( 2 ) INFORMATION FOR SEQ ID NO:55:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:55:

CCGGGATCCA ACACCCAACC ACCAACTTA                                     29

( 2 ) INFORMATION FOR SEQ ID NO:56:

( i ) SEQUENCE CHARACTERISTICS:
        ( A ) LENGTH: 52 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:56:

GCACGGGAGC TCATTAACCC TCACTAAAGG GACACAACAA AGGAACCAAA TG            52

( 2 ) INFORMATION FOR SEQ ID NO:57:

( i ) SEQUENCE CHARACTERISTICS:

(A) LENGTH: 56 base pairs
(B) TYPE: nucleic acid
(C) STRANDEDNESS: single
(D) TOPOLOGY: linear (i i) MOLECULE TYPE: DNA (genomic)

(x i) SEQUENCE DESCRIPTION: SEQ ID NO:57:

```
GCACCGGGAT CCAATTTAAT ACGACTCACT ATAGGGAACA CCCAACCACC AACTTA         56
```

(2) INFORMATION FOR SEQ ID NO:58:

(i) SEQUENCE CHARACTERISTICS:
(A) LENGTH: 78 amino acids
(B) TYPE: amino acid
(C) STRANDEDNESS: single
(D) TOPOLOGY: linear (i i) MOLECULE TYPE: peptide (x i) SEQUENCE DESCRIPTION: SEQ ID NO:58:

```
Met Glu Arg Ser Ser Asn Glu Val Ser Asn Pro Val Ala Gly Asn Phe
 1               5                  10                  15

Val Phe Pro Ser Asn Ala Thr Phe Met Gly Asp Arg Val Arg Lys
                20                  25                  30

Lys Ser Gly Ala Ala Trp Gln Gly Gln Ile Val Gly Trp Tyr Cys Thr
             35                  40                  45

Asn Leu Thr Pro Glu Gly Tyr Ala Val Glu Ser Glu Ala His Pro Gly
         50                  55                  60

Ser Val Gln Ile Tyr Pro Val Ala Ala Leu Glu Arg Ile Asn
65                  70                  75
```

(2) INFORMATION FOR SEQ ID NO:59:

(i) SEQUENCE CHARACTERISTICS:
(A) LENGTH: 286 base pairs
(B) TYPE: nucleic acid
(C) STRANDEDNESS: single
(D) TOPOLOGY: linear (i i) MOLECULE TYPE: DNA (genomic)

(x i) SEQUENCE DESCRIPTION: SEQ ID NO:59:

```
GAGCTCCACA ACAAAGGAAC CAAATGGAAC GAAGTAGCAA TGAAGTCAGT AATCCAGTTG     60
CTGGCAATTT TGTATTCCCA TCGAACGCCA CGTTTGGTAT GGGAGATCGC GTGCGCAAGA   120
AATCCGGCGC CGCCTGGCAA GGTCAGATTG TCGGGTGGTA CTGCACAAAT TTGACCCCCG   180
AAGGCTACGC CGTCGAGTCT GAGGCTCACC CAGGCTCAGT ACAGATTTAT CCTGTTGCGG   240
CGCTTGAACG CATCAACTAA TAAGTTGGTG GTTGGGTGTT GGATCC                  286
```

(2) INFORMATION FOR SEQ ID NO:60:

(i) SEQUENCE CHARACTERISTICS:
(A) LENGTH: 286 base pairs
(B) TYPE: nucleic acid
(C) STRANDEDNESS: single
(D) TOPOLOGY: linear (i i) MOLECULE TYPE: mRNA (x i) SEQUENCE DESCRIPTION: SEQ ID NO:60:

```
GAGCUCCACA ACAAAGGAAC CAAAUGGAAC GAAGUAGCAA UGAAGUCAGU AAUCCAGUUG     60
CUGGCAAUUU UGUAUUCCCA UCGAACGCCA CGUUUGGUAU GGGAGAUCGC GUGCGCAAGA   120
AAUCCGGCGC CGCCUGGCAA GGUCAGAUUG UCGGGUGGUA CUGCACAAAU UUGACCCCCG   180
```

```
AAGGCUACGC CGUCGAGUCU GAGGCUCACC CAGGCUCAGU ACAGAUUUAU CCUGUUGCGG      240

CGCUUCUCGA ACGCAUCAAC UAAGUUGGUG GUUGGGUGUU GGAUCC                    286
```

( 2 ) INFORMATION FOR SEQ ID NO:61:

( i ) SEQUENCE CHARACTERISTICS:
        ( A ) LENGTH: 78 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:61:

```
Met Glu Arg Ser Ser Asn Glu Val Ser Asn Pro Val Ala Gly Asn Phe
 1               5                  10                  15

Val Phe Pro Ser Asn Ala Thr Phe Gly Met Gly Asp Arg Val Arg Lys
            20                  25                  30

Lys Ser Gly Ala Ala Trp Gln Gly Gln Ile Val Gly Trp Tyr Cys Thr
        35                  40                  45

Asn Leu Thr Pro Glu Gly Tyr Ala Val Glu Ser Glu Ala His Pro Gly
    50                  55                  60

Ser Val Gln Ile Tyr Pro Val Ala Ala Leu Glu Arg Ile Asn
65                  70                  75
```

( 2 ) INFORMATION FOR SEQ ID NO:62:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:62:

```
GAGCTCCACA ACAAAGGAAC CAAATG                                           26
```

( 2 ) INFORMATION FOR SEQ ID NO:63:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:63:

```
GCGCACGCGA TCTCCC                                                      16
```

( 2 ) INFORMATION FOR SEQ ID NO:64:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:64:

```
CTCGACGGCG TAGCCT                                                      16
```

( 2 ) INFORMATION FOR SEQ ID NO:65:

(i) SEQUENCE CHARACTERISTICS:
    (A) LENGTH: 26 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:65:

GGATCCAACA CCCAACCACC AACTTA                                    26

METHOD FOR HYPERMUTAGENESIS OF NUCLEOTIDES

BACKGROUND OF THE INVENTION

The present invention relates to a method for introducing in vitro multiple mutations into a DNA or RNA sequence of interest or a target DNA or RNA sequence hereinafter called the technique of hypermutagenesis. More specifically, the present invention relates to a method for producing a collection of hypermutated genomic DNA, cDNA and RNA sequences in a simple one step reaction. The present invention further relates to the use of the method of the present invention to develop novel polypeptides, peptides, or improved genetic expression systems for biotechnical applications. The present invention also relates to antibodies produced against the mutated polypeptides and to the use of said polypeptides in diagnosis and vaccination fields or in gene therapy or for therapeutic purposes. The method of the present invention can also be used for identification of functionally important regions in proteins and gene regulatory regions.

Proteins and peptides play an essential role in all biochemical and many pharmaceutical applications. The primary structure of a polypeptide, as encoded by its respective gene, contains the determinants for its folding to a specific three-dimensional structure and also for all of its properties. Therefore, by changing the base sequence of the respective gene, all properties of a protein can be in principle modified towards a desired optimum. Gradual accumulation of random base substitution mutations is an essential mechanism that creates genetic diversity, which serves as material for genetic selection under various conditions during the development of novel proteins for technical applications. The essential features of such methods include the random and efficient generation of base substitutions and the optimization of the ratio between the twelve different types of base substitutions.

Until a few years ago, only two methods were available to directly study the relationship between the structure and function of a protein. These methods included the chemical modification of the side chains of amino acids that form the primary sequence of the protein and X-ray diffraction of protein crystals. There were, however, problems associated with these two methods which problems included the fact that the proteins had to be available in large quantity and be of high purity.

A variety of different methods have been recently developed for studying the relationship between the structure and function of a protein by introducing mutations into cloned genes and screening for specific properties of the proteins generated by the mutations. All of these methods involve the use of enzymes and chemicals that cleave, degrade or synthesize DNA. For example, the previously described random in vitro mutagenesis methods include the use of mutagenic chemicals (Myers et al. *Science*, 229 pp. 242–249 (1985)), oligonucleotide mutagenesis of heteroduplex or cassette type (Hutchinson et al., *PNAS*, U.S.A., 83, pp. 710–714 (1986)), enzymatic misincorporation (Shortle and Lin, *Genetics* 110, pp. 539–555 (1985)), and the enzymatic random mutagenesis method described by Lehtovaara et al., *Protein Engineering*, vol. 2, no. 1 pp. 63–68 (1988).

The problems encountered with the above-mentioned methods are multifold. First of all, many of the above-described methods are laborious, result in incomplete libraries, are expensive or are not efficient enough to permit complex screening systems for randomly mutagenized genes and their protein products. For example, in oligonucleotide-mediated mutagenesis, the larger and more complex the mutation, the lower the efficiency with which it will be generated. It is known that when large deletions are generated approximately 50-fold lower efficiency occurs than in mutations involving only local changes in sequences.

Moreover, the frequencies of mutations of the closest prior art methods are on the order of $10^{-3}$ to $10^{-4}$ per base, which is quite low. The number of mutated clones resulting from these procedures is at best about 60% or less, while the number of mutations per clone is usually less than or equal to 2.

For example, EP 0 285 123 describes a method of generating one or two point mutations in each mutant and generating a library containing all possible single base mutations of a gene by a process that involves limited elongation of a primer, enzymatic misincorporation using Klenow polymerase to generate point mutations into the molecular population, and completion of the mutagenized molecules in forms that can be amplified and further isolated by molecular cloning. The frequency of the mutants generated by this method is about 60% with each mutant containing on the average 1.8 base substitutions.

Pjura et al. in *Protein Science*, 2, pp. 2217–2225 (1993) describe a misincorporation mutagenesis method using a single-stranded phage M13mp18 and avian myeloma virus reverse transcriptase to identify thermostable mutants of T4 lysozyme. However, one of the problems with this assay was that mutations occurred outside the intended area of the M13 genome targeted by the initial primer-extension reaction, i.e., in the lac operator gene. In addition, the overall mutation rate remained low.

Therefore, there is a need in this art to generate a method to mutate cDNA sequences that is efficient, practical, and overcomes the problems associated with the known prior art methods.

RNA viruses replicate with an intrinsic error some 300 times greater than DNA based microbes and approximately $10^6$ times greater than eukaryotic genomes. See, Drake, *PNAS, USA* 90 pp. 4171–4175 (1993). This is a consequence of total lack of replication proofreading machinery and results in an intrinsic nucleotide substitution error of about 0.05 to 1 per genome per cycle. See, Holland et al., *Curr. Top. Microbiol. Immunol.*, 176, pp. 1–20 (1992). Occasionally, there is a total breakdown in replication fidelity giving rise to hypermutated genomes encoding hundreds of monotonously substituted bases. See, for example Vartanian et al. *PNAS, USA*, 91 pp. 3092–3096 (1994).

To date there are two different types of known hypermutated RNA viral genomes. Adenosine (A)→Inosine (I) hypermutation of measles and vesicular stomatitis viral genomes, which are thought to result from post-transcriptional enzymatic modification of adenosine to inosine. Bass et al., *Cell*, 56, 331 (1989). G→A hypermutated genomes have been described for a large number of lentiviruses including human immunodeficiency virus type 1 (HIV-1) and were hypothesized to arise during reverse transcriptase as a result of monotonous substitution of dCTP by dTTP due to the localized depletion of intracellular dCTP (deoxycytidine triphosphates). Vartanian et al., *J. Virol.* 65, pp. 1779–1788 (1991); Vartanian et al. (supra).

While saturation mutagenesis would allow libraries of mutants to be made and screened for desired properties, invariably only single or at most double mutations are introduced so restricting the sequence space that may be explored. The present invention started to evolve from the fact that hypermutated sequences naturally occur during reverse transcription in HIV-1 and were possibly due to the depletion of intracellular dCTP. See, for example, the Abstract by Martinez et al., "Hypermutagenesis of RNA using HIV-1 Reverse Transcriptase and Biased dNTP Concentrations", Retroviruses, May 25, 1994. The finding of G→A hypermutated retroviral genomes in which up to 40% of guanines may be substituted adenines suggested a means to hypermutagenize nucleic acids. While G→A hypermutation was suggested to result from the fluctuation in the intracellular dCTP concentration, attempts to reproduce such phenomena either in vivo by the modulation of intracellular pools using low reverse transcriptase (RTase)/template ratios have not met with success.

SUMMARY OF THE INVENTION

Generally, the method of the present invention involves transcribing a RNA into a DNA using any reverse transcriptase, including those derived from a lentivirus or a hepadnavirus, for example, and using various biased concentrations of deoxynucleoside triphosphates to produce hypermutations. Using a reverse transcriptase/template molar ratio of ~30:1, comparable to that within the retroviral replication complex, and highly biased dNTP concentrations, hypermutants can be produced in a simple in vitro reaction using a RNA template and reverse transcriptase (RTase). T→C hypermutants can be produced by using low dCTP/high dTTP and low dATP/high dGTP, respectively, the degree of hypermutation being inversely proportional to the concentration of dCTP or dATP used. Mixed G→A and T→C hypermutants can also be produced under conditions of low dCTP+dATP and high dTTP+dGTP. The DNA is recovered and may be PCR amplified, cloned into an expression vector, expressed in a suitable host microorganism, and screened for appropriate traits that may have been generated by the hypermutation.

The simplicity of the method of the invention allows the exploration of sequence space to greater degrees than heretofore, and in conjunction with genetic screening, is of use in the search of proteins with novel or enhanced properties.

Accordingly, it is an object of the present invention to provide a method to produce a collection of hypermutated cDNA, genomic DNA, and RNA sequences much more efficiently and in greater quantity and with a greater mutation frequency than those presently described in the prior art.

Yet another object of the present invention is to provide a method to produce a collection of hypermutated cDNA, genomic DNA, and RNA sequences that can be produced in a simple one or two step reaction and to introduce mutations into cDNA, genomic DNA and RNA.

Yet another object of the present invention is to provide novel polypeptides and improved genetic expression systems by using the method of the present invention.

Yet another object of the present invention is to produce monotonous nucleic acid substitutions in the DNA sequence of interest of G→A or U/T→C using one strand of RNA template, or A→G or C→T using the opposite strand of the RNA template.

It is yet another object of the present invention to produce mixed mutations of the DNA sequence of interest involving the nucleic acid substitutions of G→A and U/T→C or A→G and C→T.

In another aspect, the present invention relates to the use of a reverse transcriptase such as a lentiviral or a hepadnaviral reverse transcriptase or a retroviral reverse transcriptase in the present process capable of introducing a frequency of mutation in a target nucleotide sequence between $10^{-1}$ and $10^{-3}$, to transcribe in vitro RNA into a DNA.

The present invention features a method for introducing hypermutations into a target DNA or RNA sequence of interest, wherein the method comprises the steps of:

(a) transcribing a RNA into DNA in a reaction mixture comprising a reverse transcriptase, varying biased concentrations of deoxynucleoside triphosphates to produce hypermutations, and an oligonucleotide primer that is partially complementary to the 3' end of the RNA; and (b) recovering the DNA sequences.

In a preferred embodiment, the present invention features a method for introducing hypermutations into a target DNA or RNA sequence, wherein the method comprises the steps of:

(a) cloning the target DNA sequence into a vector that is capable of regenerating RNA in vitro;

(b) transcribing the RNA into DNA in a reaction mixture comprising a reverse transcriptase, preferably a lentivirus reverse transcriptase or a hepadnavirus reverse transcriptase, varying biased concentrations of deoxynucleoside triphosphates to produce hypermutations and an oligonucleotide primer that is partially complementary to the 3' end of said RNA; and (c) recovering the DNA sequences.

In yet another preferred embodiment, the present invention features a method for introducing hypermutations into a DNA or RNA sequence of interest, wherein the method comprises the steps of:

(a) amplifying the target DNA or RNA using oligonucleotide primers encoding promoter sequences for T7 and T3 RNA polymerases to produce RNA derived from the amplified products;

(b) transcribing the RNA into DNA in a reaction mixture comprising a reverse transcriptase, preferably a lentivirus reverse transcriptase or a hepadnavirus reverse transcriptase, with varying biased concentrations of deoxynucleoside triphosphates to produce hypermutations and an oligonucleotide primer that is partially complementary to the 3' end of the RNA; and (c) recovering the DNA sequences.

BRIEF DESCRIPTION OF THE DRAWINGS

This invention will be described in greater detail by reference to the drawings in which:

Figure 2A-1:
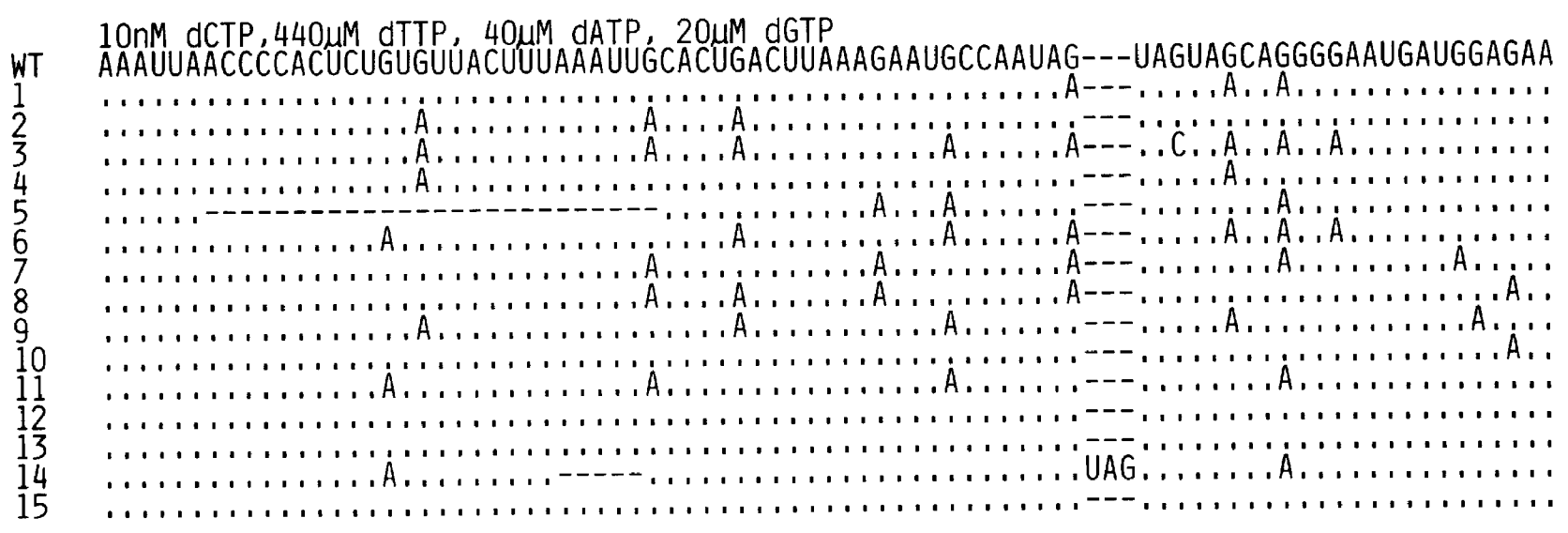
Figure 2A-2:
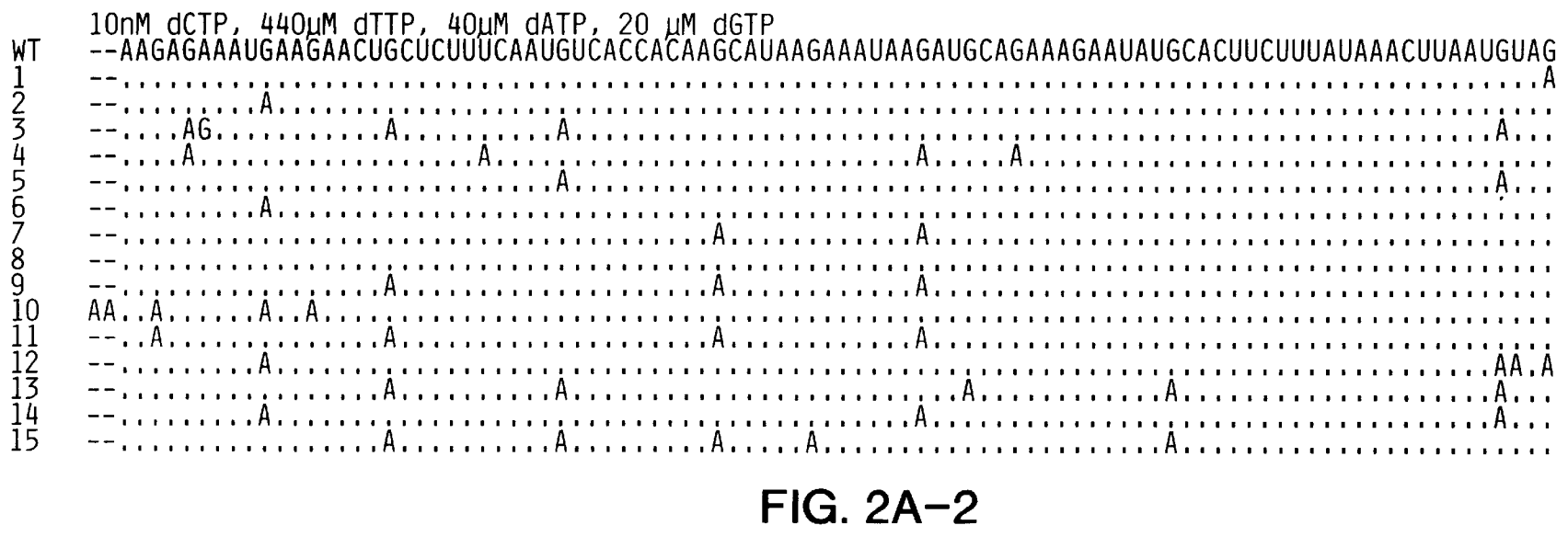
Figure 2B-1:
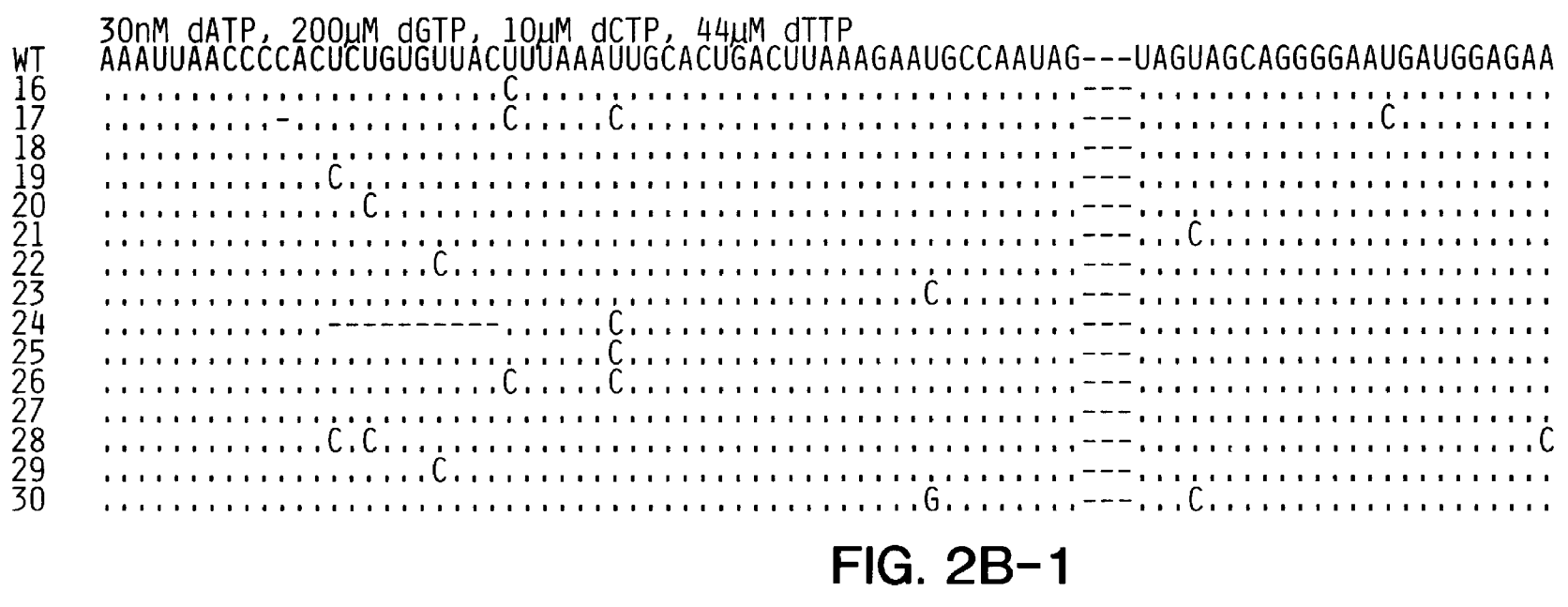
Figure 2B-2:
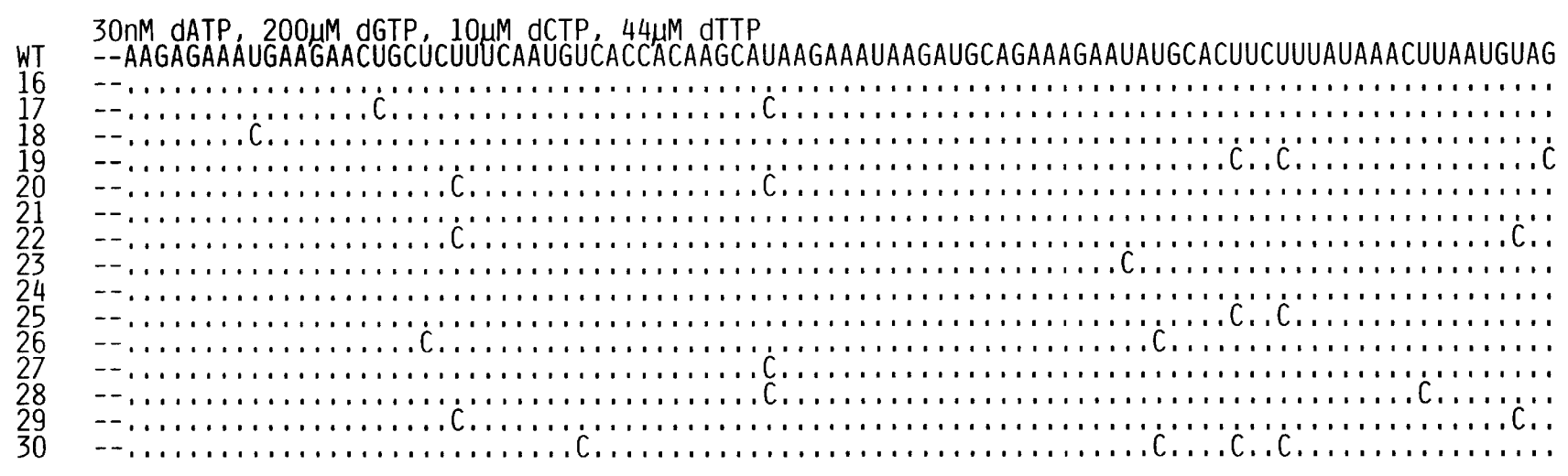

FIG. 2 illustrates the nucleic acid sequences of cDNA produced by the method of the present invention at varying deoxynucleoside triphosphate concentrations.

Lines labelled "WT" correspond to (SEQ. ID. NO:8);
line labelled "1" corresponds to (SEQ. ID. NO:9);
line labelled "2" corresponds to (SEQ. ID. NO:10);
line labelled "3" corresponds to (SEQ. ID. NO:11);
line labelled "4" corresponds to (SEQ. ID. NO:12);
line labelled "5" corresponds to (SEQ. ID. NO:13);
line labelled "6" corresponds to (SEQ. ID. NO:14);
line labelled "7" corresponds to (SEQ. ID. NO:15);
line labelled "8" corresponds to (SEQ. ID. NO:16);

line labelled "9" corresponds to (SEQ. ID. NO:17);
line labelled "10" corresponds to (SEQ. ID. NO:18);
line labelled "11" corresponds to (SEQ. ID. NO:19);
line labelled "12" corresponds to (SEQ. ID. NO:20);
line labelled "13" corresponds to (SEQ. ID. NO:21);
line labelled "14" corresponds to (SEQ. ID. NO:22);
line labelled "15" corresponds to (SEQ. ID. NO:23);
line labelled "16" corresponds to (SEQ. ID. NO:24);
line labelled "17" corresponds to (SEQ. ID. NO:25);
line labelled "18" corresponds to (SEQ. ID. NO:26);
line labelled "19" corresponds to (SEQ. ID. NO:27);
line labelled "20" corresponds to (SEQ. ID. NO:28);
line labelled "21" corresponds to (SEQ. ID. NO:29);
line labelled "22" corresponds to (SEQ. ID. NO:30);
line labelled "23" corresponds to (SEQ. ID. NO:31);
line labelled "24" corresponds to (SEQ. ID. NO:32);
line labelled "25" corresponds to (SEQ. ID. NO:33);
line labelled "26" corresponds to (SEQ. ID. NO:34);
line labelled "27" corresponds to (SEQ. ID. NO:35);
line labelled "28" corresponds to (SEQ. ID. NO:36);
line labelled "29" corresponds to (SEQ. ID. NO:37);
line labelled "30" corresponds to (SEQ. ID. NO:38);
line labelled "31" corresponds to (SEQ. ID. NO:39);
line labelled "32" corresponds to (SEQ. ID. NO:40);
line labelled "33" corresponds to (SEQ. ID. NO:41);
line labelled "34" corresponds to (SEQ. ID. NO:42);
line labelled "35" corresponds to (SEQ. ID. NO:43);
line labelled "36" corresponds to (SEQ. ID. NO:44);
line labelled "37" corresponds to (SEQ. ID. NO:45);
line labelled "38" corresponds to (SEQ. ID. NO:46);
line labelled "39" corresponds to (SEQ. ID. NO:47);
line labelled "40" corresponds to (SEQ. ID. NO:48);
line labelled "41" corresponds to (SEQ. ID. NO:49);
line labelled "42" corresponds to (SEQ. ID. NO:50);
line labelled "43" corresponds to (SEQ. ID. NO:51);
line labelled "44" corresponds to (SEQ. ID. NO:52);
line labelled "45" corresponds to (SEQ. ID. NO:53);

FIG. 3 illustrates the forward (SEQ. ID. NO:54) and backward (SEQ. ID. NO:55) primer sequences utilized in the method of the present invention for the R67 gene.

FIG. 4 illustrates the forward (SEQ. ID. NO:56) and backward (SEQ. ID. NO:57) primer sequences containing T3 and T7 promoter sequences for PCR amplification.

FIG. 5 is the DNA (SEQ. ID. NO:59) and amino acid (SEQ. ID. NO:58) sequences of a R67 gene that can be hypermutated by the methods in the present invention.

Figure 6:
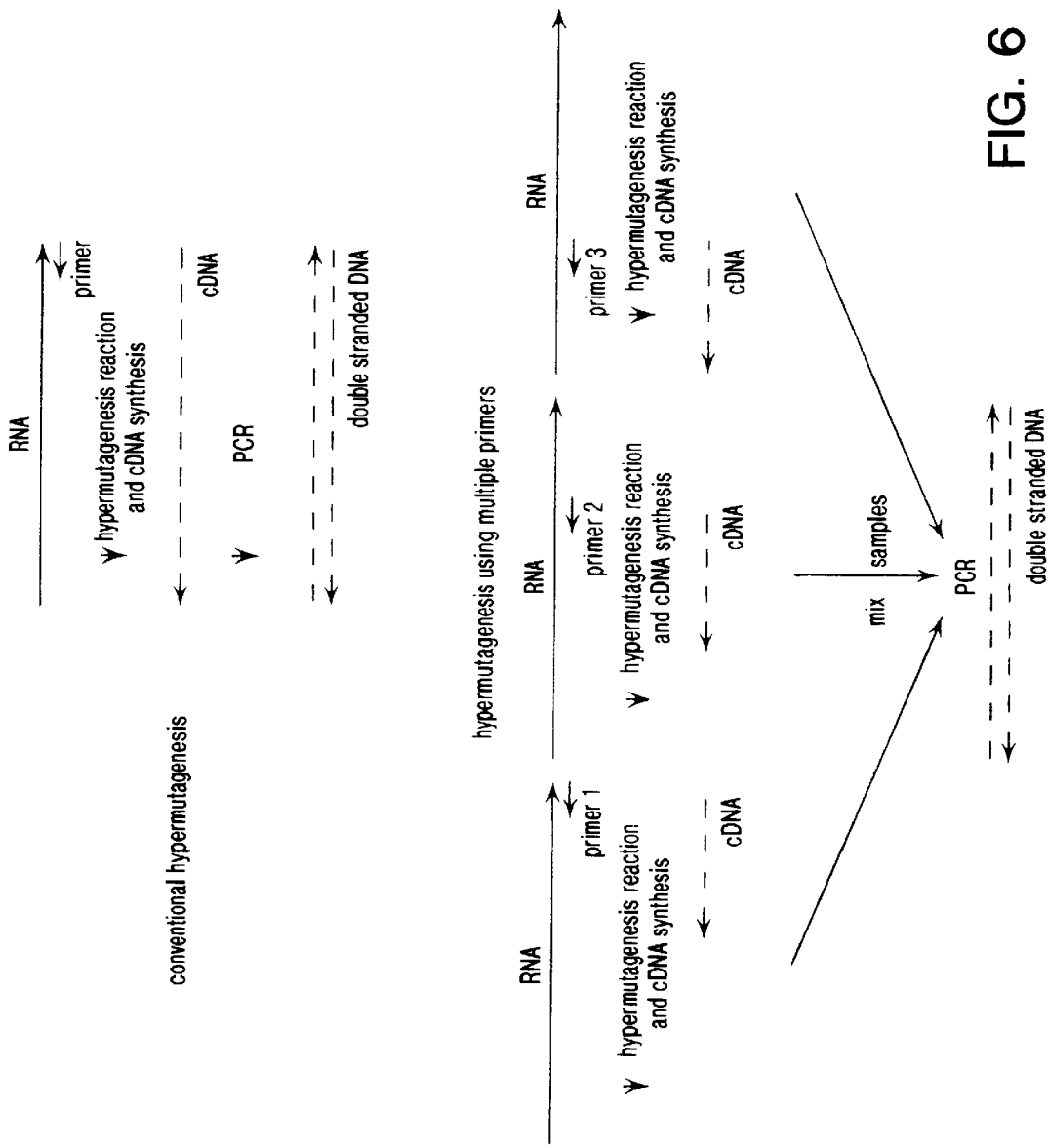

FIG. 6 depicts a modification of the invention in which multiple primers are used to increase the efficiency of cDNA synthesis during the hypermutagenesis reaction.

FIG. 7 depicts the use of multiple primers according to the technique of FIG. 6 to hypermutate the R67 gene. Modified R67 gene sequence with respect to that given in Brisson and Hohn, Gene 28, 271–275, 1984 is shown in FIG. 7. Amino acid sequence (SEQ. ID. NO:61) in the three letter code is given above the nucleic acid sequence (SEQ. ID. NO:60). Primer 1 corresponds to (SEQ. ID. NO:63); primer 2 corresponds to (SEQ. ID. NO:64); primer 3 corresponds to (SEQ. ID. NO:65); primer 4 corresponds to (SEQ. ID. NO:62).

Figure 8:
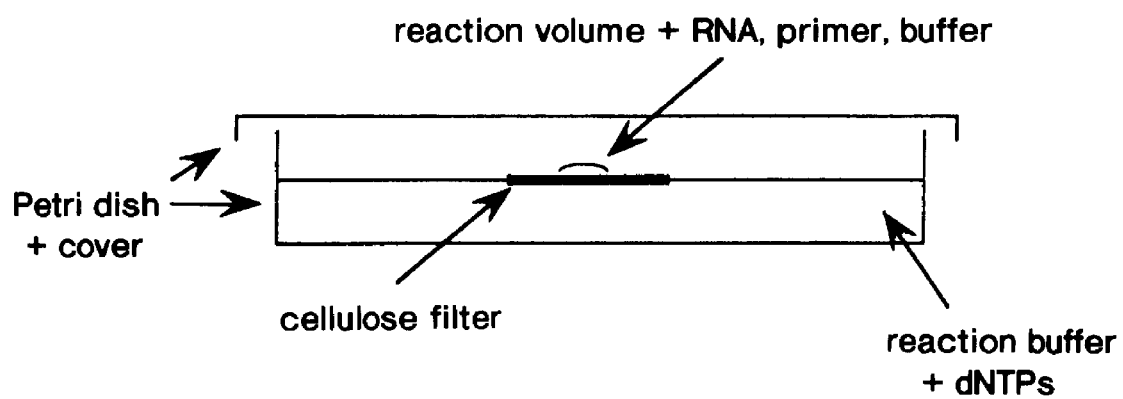

FIG. 8 is a diagram of another modification of the invention using dialysis to increase the efficiency of cDNA synthesis during the hypermutation reaction.

DESCRIPTION OF THE PREFERRED EMBODIMENTS

The present invention relates to a process for generating a library of hypermutant DNA sequences that differ from the natural DNA sequences by changes made in nucleotide base pairs. Mutant proteins with the desired properties can be identified and expressed in a suitable host. Specific conditions can then be designed to screen the transformants for the particular trait in question.

As used herein the term "hypermutated" means that the DNA sequence has at least three base pair changes that differ from the unmutated DNA sequence.

As used herein, the term "varying concentrations of deoxynucleoside triphosphates" means differing concentrations of dCTP, dTTP, dATP, and dGTP.

As used herein, the term "biased pyrimidine concentrations" means the concentration ratio of dCTP to dTTP in the reaction mixture is not equal or is unbalanced. For example, there is a low concentration of dCTP and a high concentration of dTTP.

As used herein, the term "biased purine concentrations" means that the concentration ratio of dATP and dGTP in the reaction mixture is not equal or is unbalanced. For example, there is a low concentration of dATP and a high concentration of dGTP.

As used herein, the term "partially complementary" when referring to the oligonucleotide primers means that the oligonucleotide sequence does not have to be 100% complementary to the RNA sequence; i.e., that each nucleotide need correspond to the complementary nucleotide. It is preferable that at least 10 nucleotides are complementary and more preferably from about 15 to 20.

As used herein, the word "unmutated" encompasses, any natural nucleic acid sequence or a genetically engineered or chemically modified nucleic acid sequence, which sequences have not been hypermutated.

The term "base pairs" means normal or analogous molecules used in nucleotide sequences.

The term "natural DNA sequence" connotes that the DNA sequence is one that is not altered from that found in nature.

As used herein, the symbol "G→A", when referring to hypermutations, means that a guanine-based nucleotide is substituted by an adenine-based nucleotide.

As used herein, the symbol "U→C" when referring to hypermutations means that a uracil-based nucleotide is substituted by a cytidine-based nucleotide.

Also contemplated by the present invention is the use of the process of hypermutagenesis to modify any protein such as enzymes, receptors, restriction enzymes, monoclonal or polyclonal antibodies, nucleic acid polymerases (i.e., reverse transcriptase), and the like to confer on the protein different properties from the natural properties of the protein. For example, the modification by hypermutagenesis of restriction enzyme genes may result in restriction enzymes having novel restriction sites. A monoclonal antibody can be altered by hypermutagenesis to improve its affinity. The catalytic site of an enzyme can be hypermutated to improve its catalytic activity or alter its substrate specificity.

Thus, for example, modified subtilisin in which two amino acids have been altered to produce subtiligase has recently been used for the total synthesis of a variant of ribonuclease A containing non-natural catalytic residues. See, *Science,* 226, 243 (1994). Such modified proteins can be produced by the process of hypermutagenesis of the present invention.

Also contemplated by the present invention are antibodies produced against the mutated polypeptides and to the use of said polypeptides for diagnosis and vaccination fields or gene therapy or therapeutics. Novel forms of antibiotics are also contemplated by the present invention and can be obtained by hypermutating the genes involved in the biosynthesis of presently known antibiotics. Other uses of the novel proteins produced by the method of the present invention are also contemplated but are too numerous to mention.

Generally, the present invention involves the production of a hypermutated DNA sequence by starting with, for example, mRNA isolated from total RNA of the sequence of a target DNA sequence or fragment of interest. By target DNA sequence or DNA sequence of interest is meant any DNA sequence that is or will be known in the art that can be subjected to the hypermutagenesis process, such as cDNA and genomic DNA. RNA can be subjected to hypermutation, also. The choice of the target DNA or RNA sequence depends, of course, on the type of mutant one wants to create and the type of trait one wants to instill on the protein.

The various types of DNA or RNA sequences include, but are not limited to, DNA sequences of enzymes, restriction enzymes, nucleic acid polymerases, monoclonal or polyclonal antibodies, genes involved in the synthesis of antibiotics, gene transfer vector sequences, and the like, as well as fragments of these sequences. It is well within the knowledge of a person skilled in the art to choose the target DNA sequences.

Total RNA can be isolated by a variety of methods known in the art, such as proteinase K digestion, followed by phenol:chloroform extraction, guanidinium thiocyanate extraction, followed by cesium chloride gradients, guanidine hydrochloride and organic solvent extraction, and the like.

mRNA can then be isolated from total RNA by methods known in the art. These methods include the use of oligo (dT)-cellulose, poly(U) Sepharose, adsorption to and elution from poly(U) filters or nitrocellulose membrane filters, and the like. It is preferable to use oligo(dT) cellulose chromatography in isolating mRNA following the procedure described by Sambrook et al., *Molecular Cloning*, A Laboratory Manual (1989).

Alternatively, a DNA sequence of interest or a fragment thereof can be purified by methods known in the art and cloned into a plasmid or phage vector that is capable of generating RNA in vitro that is complementary to either of the two strands of foreign DNA inserted into the polycloning site. Preferred vectors of the present invention include pGEM-3, pGEM-4, pGEM-3Z, pGEM-3Zf(−), Bluescript M13⁻, Bluescript M13⁺, pBluescript SK⁺, Bluescript KS⁺, and variations thereof. It is preferable to use a vector that has a promoter on each side of the polycloning site; these promoters include the T7 promoter, the SP6 promoter, the T3 promoter and the like.

The RNA of interest can be generated by using the insert DNA as a template for in vitro transcription using a RNA polymerase. Any RNA polymerase can, in principle, be used, such as RNA polymerase I, RNA polymerase II, RNA polymerase III, T7 RNA polymerase, T3 RNA polymerase, SP6 RNA polymerase, and the like, provided that the corresponding promoter sequences flank the target sequence. It is most preferable to use T7 RNA polymerase.

The reaction conditions for generating RNA in a plasmid can vary according to the vector system and DNA insert. These reaction conditions are well known in the art and can be adjusted accordingly to optimize the production of RNA.

One preferred example of the reaction conditions is: 500 $\mu$M each of deoxynucleoside triphosphates, 100 ng of template, 0.3 U/$\mu$l of RNase inhibitor and 2U/$\mu$l of RNA polymerase, and buffer in a final volume of 100 $\mu$l. After the RNA is produced, it can then further purified by phenol extraction and ethanol precipitation according to Sambrook et al. (supra).

In another preferred embodiment of the present invention, the target DNA can be PCR amplified using oligonucleotide primers encoding the promoter sequences for the T7, SP6, and T3 RNA polymerases. Thus, RNA can be derived directly from the amplified products without resorting to an intermediate cloning step. Examples of these T7 and T3 RNA polymerase primers for use in this embodiment are exemplified in FIG. 4.

Thus, RNA can be obtained by any method, said RNA corresponding to the target DNA sequence of interest. After acquiring the RNA or mRNA by the various methods set forth above, the RNA or mRNA is then transcribed into DNA by using a reverse transcriptase, and varying biased concentrations of deoxynucleoside triphosphates to produce hypermutation, and an oligonucleotide primer under conditions allowing the favorable transcription of RNA into DNA in a reaction mixture.

Any reverse transcriptases can be utilized in the present invention. Such reverse transcriptase can be isolatable from a retrovirus capable of infecting eukaryotic cells. For example, these reverse transcriptases include human immunodeficiency virus Type 1 (HIV-1) reverse transcriptase, human immunodeficiency virus Type 2 (HIV-2) reverse transcriptase, simian immunodeficiency virus reverse transcriptase, feline immunodeficiency virus reverse transcriptase, reverse transcriptase derived from the ungulate lentiviruses, and lentivirus reverse transcriptases that are hypermutated variations of the lentivirus reverse transcriptase. It is preferable to use HIV-1 reverse transcriptase or HIV-2 reverse transcriptase in the transcription method of the present invention.

The invention concerns itself particularly with lentiviral reverse transcriptases. However, it is known that the reverse transcriptases of avian myeloblastosis virus and Moloney murine leukemia virus are capable of hypermutagenizing RNA also. In the current protocol they are not capable of the same degree of mutation. Nonetheless they, as well as reverse transcriptases derived from other retroviruses, are useful reagents and can be utilized in the present method.

Reverse transcriptases also associated with the hepadnaviruses (e.g., Human hepatitis B virus (HBV), Woodchuck hepatitis virus (WHV), Ground squirrel hepatitis virus (GSHV), Duck hepatitis B virus (DHBV), and Heron hepatitis B virus (HHBV), or with cauliomoviruses (e.g., cauliflower mosaic virus (CaMV)) can also be utilized. Thus, the above-described reverse transcriptases from these viruses are useful reagents and can be utilized in the present method.

Other DNA dependent DNA polymerases, which possess a reverse transcriptase activity under standard or modified experimental conditions, could, in principle, also be used. Examples include Tth, TetZ, thermostable polymerases, or Klenow enzyme.

The amount of reverse transcriptase utilized in the reaction mixture of the present invention should be in a large molar excess in respect to the RNA. The ratio of molar excess of reverse transcriptase to RNA can vary from about 30:1 to about 50:1 (reverse transcriptase:RNA template molar ratio). It is preferable to use about a 50:1 molar excess. For example, if 0.5 pmol of RNA template is utilized, the reverse transcriptase is present in the reaction mixture on the order of between about 15.0 pmol to about 25.0 pmol.

The reverse transcriptase catalyzes the joining of deoxyribonucleotides onto the 3' OH terminus of an oligonucleotide primer. The oligonucleotide primer employed in this invention can be an oligoribonucleotide or deoxyribonucleotide. An oligonucleotide primer that is partially complementary to the 3' end the target RNA is selected on the basis of the corresponding target RNA sequence and is utilized in the reaction mixture for the transcription reaction. This oligonucleotide primer can vary in length from about 15 to about 50 nucleotides. The primer should match with about 10 to 15 nucleotides of the complementary target sequence. These oligonucleotide primers can be prepared by methods known in the art and disclosed by Sambrook et al. (supra). The concentration of the oligonucleotide primer should be in molar excess of the target RNA concentration. However, usually about 2 pmol is utilized in the reaction mixture as described below. The size of the primer, the degree of homology of the primer with the template strand, and the concentration of primer in the reaction mixture must be sufficient to enable the linking of deoxyribonucleoside 5' triphosphate to the 3' OH terminus of the primer to enable primer extension and elongation of the strand copied from the template.

Varying molar concentrations of deoxynucleoside triphosphates are then added in the transcription reaction mixture. The concentration and type of deoxynucleoside triphosphates can vary depending on the type of hypermutation in the DNA sequence of interest one wants to obtain. For example, if one wants to obtain a G→A hypermutation, then a low molar concentration of dCTP substrate is used compared to dTTP, which is used in a high molar concentration. By altering the dATP/dGTP molar ratios, i.e., using a low concentration of dATP compared to dGTP, which is used in a high concentration, hypermutation of U→C can be seen. These above-described hypermutations are "monotonous hypermutations". Expressed in terms of the make-up of the cDNA encoded by the RNA template, G→A and T→C hypermutants can be produced by using low dCTP/high dTTP and low dATP/high dGTP molar ratios, respectively, the degree of hypermutation being inversely proportional to the molar concentrations of dCTP or dATP used.

It is also possible to obtain a mixture of G→A and U→C hypermutations by using a low molar ratio of dCTP/dTTP and low molar ratio of dATP/dGTP nucleotide triphosphates during cDNA synthesis. Expressed once again in terms of the make up of the cDNA encoded by an RNA template, mixed G→A and T→C hypermutants can also be produced under conditions of low dCTP+dATP and high at dTTP+dGTP molar concentrations.

The molar concentrations of the specific deoxynucleoside triphosphates will of course depend upon the type of hypermutation selected. Therefore, a very low dCTP/dTTP molar ratio of about $10^{-4}$ will produce extensive hypermutation while hundred fold less ratio of about $10^{-2}$ will produce less hypermutations. For instance, if a low degree of hypermutations (<5%) is desired, the deoxynucleoside triphosphate bias should not be too low; i.e., dCTP/dTTP should be in a molar ratio of about 1/5,000. However, if the production of a greater degree of hypermutations is desired, then, for example, the dCTP/dTTP molar ratio can vary between 1/15,000 to 1/50,000. The amount hypermutation in the target cDNA sequence can therefore be controlled by altering the ratios of dCTP/dTTP and dATP/dGTP. One can select the concentrations of the deoxynucleoside triphosphates according to the amount of hypermutations one wants in the cDNA sequence.

In a most preferred embodiment of the invention, the concentrations of deoxynucleoside triphosphates can vary from 1 nM up to 440 μM in a transcription reaction mixture. Moreover, one can generate hypermutations in a DNA or RNA of about 100% (or total target nucleotide replacement of a DNA or RNA sequence) by the method of the present invention. Therefore, if the target DNA or RNA sequence contains, for example, 200 bp, all the target nucleotides can be altered. However, it is possible to alter the DNA or RNA sequence to a lesser extent, also which can range from about 2% to about 99%, and more preferably from about 2% to about 20%. More specifically, for a G→A hypermutation, it is most preferable to use 1 to 100 nM of dCTP, about 440 μM of dTTP, about 40 μM of dATP, and about 20 μM of dGTP in the transcription reaction mixture. In contrast, for a type of hypermutation from U→C, it is most preferred to use approximately 10 μM dCTP, 44 μM of dTTP, 3 to 100 nM of dATP, and 200 μM of dGTP in the transcription reaction mixture. For a mixed type of hypermutation, that is G→A plus U→C, it is most preferable to use about 1 to 100 nM of dCTP, about 440 μM of dTTP, 1 to 100 nM of dATP, and about 200 μM of dGTP in the transcription reaction mixture.

It must be realized that there is considerable latitude in some of the dNTP concentrations. Thus in order to accomplish G→A hypermutation the key element is that the dCTP concentration must be low (1–100 nM) and the dTTP must be high (>100 μM). The concentration of dATP (40 μM) and dGTP (20 μM) were chosen as they approximate the mean intracellular concentration in mammalian lymphocytes. In this example, the only important feature of the dATP and dGTP concentrations is that they are saturating (>1–5 μM). Thus, any concentration beyond this is satisfactory.

The reverse transcriptase reaction is generally run in a reaction buffer that also can vary, e.g., according to the procedures of Sambrook et al. supra. However, it is most preferable to use a buffer consisting of 50 mM Hepes (pH 7), 15 mM Mg aspartate, 10 mM DTT, 55 mM K acetate, and 15 mM NaCl.

In a preferred embodiment of the present invention the reaction mixture for the transcription reaction consists of 0.5 pmol template RNA, 2 pmol oligonucleotide primer, in 50 μl reaction buffer, 0.3 U/ml of RNase inhibitor, and 15 pmol (6.25 units) of HIV-1 reverse transcriptase. However, the person skilled in the art can alter this reaction mixture accordingly and obtain the target cDNA according to methods known in the art.

The reverse transcriptase reaction can be carried out over a period of time that varies of course with the length of the DNA insert and the oligonucleotide primer utilized. For example, when annealing the oligonucleotide primer, 1 minute incubation at various temperatures and with various substitutes is generally performed prior to the addition of the reverse transcriptase. After the addition of the reverse transcriptase, the reaction is usually run at about 37° C. for about 3 hours. More specifically, the primers can be annealed to the template DNA by first heating to about 65° C. for 1 minute, followed by incubation at 37° C. for 1 minute, after which the reverse transcriptase is added. These reaction conditions can be adjusted to obtain optimal DNA or RNA production.

After the DNA or RNA has been generated, the DNA or RNA is recovered by any method known in the art, such as the methods described by Sambrook et al., supra, or in European Patent Application No. 518 313. More preferably, the DNA or RNA can be amplified by PCR with forward and backward primers to generate sufficient DNA to further clone into a plasmid for regeneration. One can also use the T7 and/or T3 promoter sequences in the PCR primers. This way, the target DNA or RNA sequence of interest can be cycled in the PCR process. For example, a protocol for one PCR cycle would require 1) PCR amplification of target sequence, 2) DNase treatment, 3) RNA synthesis using the T7 or T3 dependant RNA polymerases, and 4) target DNA or RNA synthesis using, for example, the lentivirus reverse transcriptase and biased dNTP pools.

Once the sequences have been hypermutated and the target DNA or RNA sequences have been sufficiently recovered, they can be further ligated into any expression vector and transformed in a host microorganism. Any expression vector known in the art can be utilized, and any host microorganism can be utilized. Examples of these systems are described by Sambrook et al., supra, or in PCT No. WO-93 19785.

Once expressed, the hypermutated DNA or RNA sequences can be screened. There are a large number of screening systems known in the art, such as genetic complementation in bacterial yeast, mammalian systems, and the like. The screening system will of course depend on the particular gene of study. For example, R67 is a dehydrogenase that specifically reduces dihydrofolate to tetrahydrofolate. If hypermutated, R67 DNA can be ligated into a expression vector such as pTrc99A and used to transform strains of *E. coli* deficient in one of many dihydrogenases. It is possible to then select for a mutant of broadened or altered specificity.

A hypermutated protein or peptide characterized by a mutation frequency between $10^{-1}$ to $10^{-3}$ as compared to the target molecule is also contemplated by the present invention. Purified monoclonal antibodies made from the hypermutated DNA sequences and immunogenetic molecules made from the process of the present invention are also contemplated.

Chimeric proteins containing mutations at least about 20%, preferably about 5% to 50% and 80%, preferably between 95 to 5% unmutated sequence are also contemplated by the present invention.

The present invention also concerns the preparation of cell lines containing the hypermutated genes carried by a vector and stably integrated into the genome.

This invention is also applicable to plant cells, plant cell cultures and nucleic acid sequences encoding plant proteins.

As discussed above, the applications of hypermutagenesis are too numerous to mention. However, useful applications of the hypermutagenesis process contemplated by the present invention are the following:

1) The modification of restriction endonuclease genes with a view to isolating restriction enzymes with novel restriction sites.

2) The modification of monoclonal antibody VH and VL genes with a view to improving the affinity of the monoclonal antibody. The affinity of monoclonal antibodies are notoriously low. Any improvement in their affinity or an increase in specificity would make possible the diminution in the quantity of monoclonal antibody used per sample/reagent/kit.

3) Modification of substrate specificity. The hypermutagenesis of a gene conferring the metabolism of some toxic product or hydrocarbon, new activities are sought by plating the library of hypermutated genes on plates containing the toxic product or hydrocarbon. The uses of such novel products in pollution control is considerable.

4) Enhanced catalytic activity. Hypermutagenesis can speed up the search for variant genes products with improved nitrogen fixing activities, photosynthetic properties, protease activity, etc.

5) Producing novel DNA-dependent DNA polymerases (e.g., *E. coli* PolI, the Klenow fragment, Taq polymerases and other thermostable enzymes), DNA-dependent RNA polymerases (e.g., bacteriophage T7, T3, SP6 enzymes), and RNA dependent DNA polymerases (e.g., reverse transcriptases from any retrovirus, Tth and TetZ thermostable enzymes, Klenow fragment (under certain conditions), that when hypermutated may yield novel variants capable of hypermutagenizing RNA/DNA more efficiently than previously described.

In the specific case of reverse transcriptases, central to the hypermutagenesis method, judicious screening following hypermutagenesis of the HIV-1 reverse transcriptase gene, or a fragment thereof, it might be possible to select for variants of reduced fidelity. Alternatively, screening for variants with an enhanced ability to elongate beyond a mismatch would be practically most useful. This is because cDNA synthesis in the presence of biased dNTP pools is rather inefficient. However, if elongation could be improved, this would enable one to go to even more biased dNTP ratios (currently 44,000 fold bias), which may be extended to beyond 400,000 fold. This would enable one to increase the average degree of hypermutation by a factor of 2 or more.

If, instead of using hypermutagenesis of the HIV-1 reverse transcriptase gene, the Taq polymerase gene was studied, then following judicious screening, it is possible to find variants of Taq with a poorer fidelity. In fact, hypermutagenesis of any of the above-mentioned polymerases might lead to a crop of variants with altered properties, i.e., increased heat stability, reduced fidelity, enhanced elongation beyond a mismatch, smaller size, more protease resistant or solvent insensitive, or combinations thereof.

6) Yet another application is the hypermutagenesis of the envelope protein of retroviral vectors altering their cell tropism. Currently, many of the retroviral vectors used employ envelope proteins of a wide tropism, i.e., they infect a wide variety of different cell types. The gene corresponding to the envelope protein, or parts thereof, is hypermutated and variants can be obtained with a more restricted tropism. Such reagents can be of use in gene therapy in that they would enable a more specific targeting of the desired gene.

7) Yet another application is the hypermutagenesis of DNA/RNA sequences derived from plants or other microorganisms.

The experimental approach to the above-mentioned applications to be exploited would follow very much the experimental protocol outlined in the present application for the hypermutagenesis of target DNA or RNA sequences or fragments of a polymerase gene.

In order to further illustrate the present invention and advantages thereof, the following specific examples are given, it being understood that the same are intended only as illustrative and in no wise limitative.

EXAMPLE 1

DNA from M13 mp18 recombinant containing the env V1–V2 regions of HIV-1 B40 (described by Vartanian et al., *J. Virol.,* 65, pp. 1779–1788 (1991)) was PCR-amplified with oligonucleotide 1 (5' GCGAAGCTT AATTTAATACGACTCACTATAGGGACAAAGCCT-AAAGCCATGTGTA) (SEQ. ID NO:1) and oligonucleotide 2 (5' GCGGAATTCTAATGTATGGGAATTGGCTCAA) (SEQ. ID NO:2). Oligonucleotide 1 contains the T7 RNA polymerase promoter sequence (underlined) allowing production of plus strand transcripts of the env VA-V2 region. The 342 bp DNA fragment, with unique HindIII and EcoRI restriction sites (bold face), was digested and ligated into a pBluescript SK$^+$ vector. The resulting plasmid was digested with HindIII and EcoRI, and the fragment was purified from a 2% agarose gel.

Insert DNA was used as template for in vitro transcription using T7 RNA polymerase. Reaction conditions were: 40 mM Tris.HCl (pH 8), 30 mM MgCl$_2$, 10 mM β-mercaptoethanol, 50 μg/ml RNase/DNase-free BSA, 500 μM each NTP, 100 ng of template, 0.3 U/μl of RNase inhibitor (Pharmacia) and 2 U/μl of T7 RNA polymerase (Pharmacia) in a final volume of 100 μl. After incubation for 1 hour at 37° C., the DNA template was digested with 0.075 U/μl RNase-free DNase I (Pharmacia) for 30 min. at 37° C. RNA was phenol extracted and ethanol precipitated.

Figure 1:
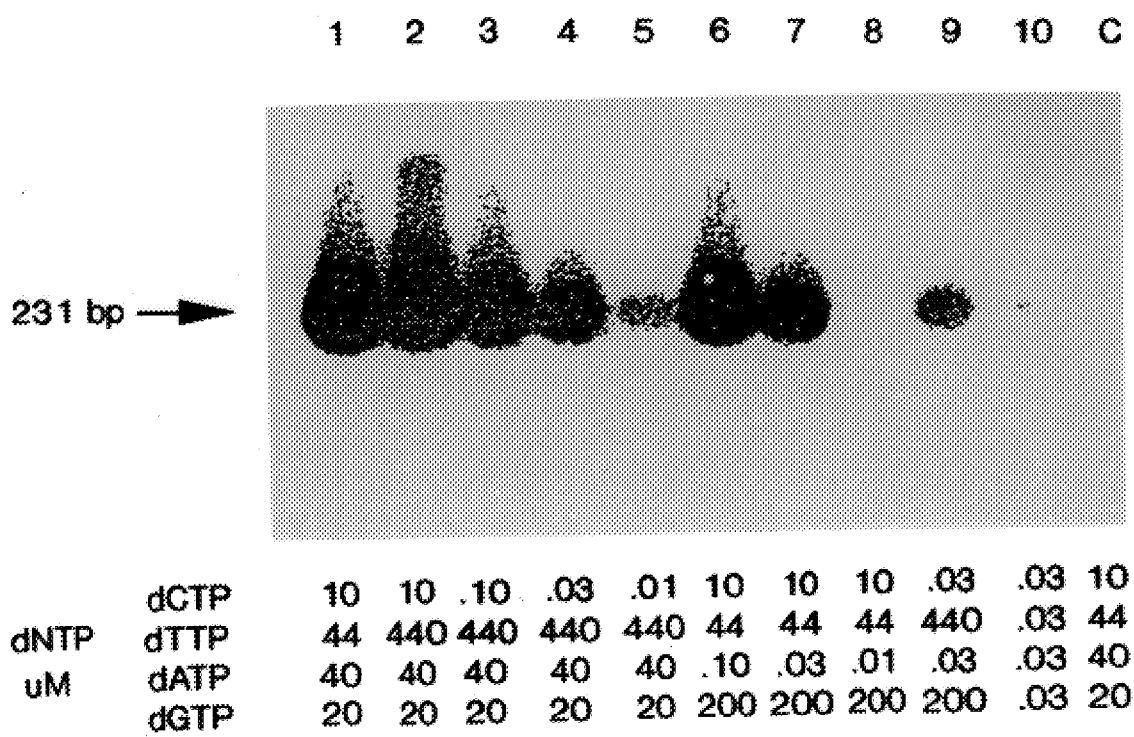
FIG. 1 is Southern Blot illustrating the efficiency of cDNA synthesis with varying concentrations of deoxynucleoside triphosphates.

The reverse transcription reaction buffer was 50 mM Hepes (pH 7), 15 mM Mg Aspartate, 10 mM DTT, 55 mM K Acetate, 15 mM NaCl, and varying dNTP concentrations (see legend to FIG. 1). Two picomoles of oligonucleotide 3 (5' GCGTCTAGAAGTATCATTATCTATTGGTA. (SEQ. ID NO:3) complementary to positions 224 to 253 of the 342 bp plus strand DNA fragment), was annealed to 0.5 pmol of the template RNA in 50 μl of the reaction by first heating to 65° C. for 1 min. followed by incubation at 37° C. for 1 min. after which 0.3 U/μl of RNase inhibitor and 15 pmol (6.25 units) of HIV-1 RTase (Boehringer) were added. The reaction was incubated at 37° C. for 3 hours.

In order to recover sufficient material for subsequent cloning, cDNA was amplified by PCR with oligonucleotide 3 and oligonucleotide 4 (5' GCGGTCGACCAAAGCCTAAAGCCA) (SEQ. ID NO:4) producing a 231 bp DNA fragment with restriction sites at its end, XbaI and SalI respectively (bold face). Optimized PCR conditions were: 2.5 mM MgCl$_2$, 50 mM KCl, 10 mM Tris.HCl (pH 8.3), 200 μM of each dNTP, 20 μl of the reverse transcription reaction and 2.5 U of Taq DNA polymerase (Cetus) in a final volume of 100 μl. Annealing, extension, and denaturation cycling parameters were: 37° C. (30s), 72° C. (30s) and 95° C. (30s) for 2 cycles and 55° C. (30s), 72° C. (30s) and 95° C. (30s) for 10 cycles. Southern blot analysis was made on 5% of the PCR amplified material electrophoresed through an agarose gel, and blotted into a nylon membrane by capillary transfer. The filter was hybridized with a $^{32}$p 5'-labelled probe 5' TGTAAAA($^T$/C) ($^T$/C) AACCCCAC($^T$/C) (SEQ ID NO:5) complementary to positions 53 to 72 of the env V1V2 342 bp minus strand. The specific 231 bp PCR fragments were purified from a 2% agarose gel, digested with XbaI and SalI and ligated into pBluescript SK$^+$ vector. Clones were dideoxysequenced using the Taq dye primer cycle sequencing kit (Applied Biosystems), with resolution of the products on a Applied Biosystems 373A sequencer. 334 recombinants were sequenced and some of the mutants sequences are shown in FIG. 2. The frequency of mutations are described in Table 1.

TABLE 1

| dNTP (μM) | | | | Plaques analyzed | | | G→A | | Deletions | Other point |
|---|---|---|---|---|---|---|---|---|---|---|
| C | T | A | G | Total | WT | Mutated | subs | fG→A* | Insertions | mutations |
| 10 | 44 | 40 | 20 | 47# | 46 | 1 | 0 | 0 | 1 | 0# |
| | | | | | | | | | 0 | |
| 1 | 440 | 40 | 20 | 90# | 78 | 12 | 12 | 4.1 × 10$^{-3}$ | 0 | 1# |
| | | | | | | | | | 0 | |
| 0.1 | 440 | 40 | 20 | 31 | 10 | 21 | 38 | 3.8 × 10$^{-2}$ | 3 | 10 |
| | | | | | | | | | 0 | |
| 0.03 | 440 | 40 | 20 | 27 | 2 | 25 | 70 | 8.1 × 10$^{-2}$ | 3 | 4 |
| | | | | | | | | | 4 | |
| 0.01 | 440 | 40 | 20 | 38 | 6 | 32 | 146 | 1.2 × 10$^{-1}$ | 3 | 10 |
| | | | | | | | | | 2 | |
| | | | | | | | U→C subs | fU→C* | | |
| 10 | 44 | 0.1 | 200 | 18 | 16 | 2 | 2 | 2.5 × 10$^{-3}$ | 0 | 0 |
| | | | | | | | | | 0 | |
| 10 | 44 | 0.03 | 200 | 33 | 6 | 27 | 58 | 4.0 × 10$^{-2}$ | 3 | 8 |
| | | | | | | | | | 0 | |
| | | | | | | | G→A U→C | fG→A fU→C | | |
| 0.03 | 440 | 0.03 | 200 | 27 | 3 | 24 | 40 | 4.6 × 10$^{-2}$ | 9 | 9 |
| | | | | | | | 24 | 2.0 × 10$^{-2}$ | 1 | |
| 0.03 | 0.03 | 0.03 | 0.03 | 22 | 19 | 3 | 1 | 1.5 × 10$^{-3}$ | 0 | 2 |
| | | | | | | | 0 | | 0 | |

EXAMPLE 2

A dihydrofolate reductase (DHFR) gene encoded by an *E. coli* plasmid R67 and will hereafter be referred to as R67 DHFR or simply R67 utilized as the target DNA sequence of interest. The corresponding coding sequences were amplified by PCR from a plasmid clone under standard conditions (2.5 mM MgCl$_2$, 50 mM Tris-HCl pH 8.3, 50 mM KCl, 200 μM each dNTP, 100 ng plasmid DNA, 100 pmol of each primer (see FIG. 3), 2.5 U Taq polymerase (Cetus); 15 cycles with the following cycling parameters; 30 sec. 92° C., 30 sec. 55° C. and 30 sec. 72° C.). The resulting product was digested with SacI and BamHI restriction endonucleases and cloned into the BlueScript vector pSK+. Recombinant clones were checked by sequencing.

RNA was derived from the cloned R67 gene sequences by using the T7 RNA polymerase in an in vitro reaction. Before the T7 reaction, supercoiled plasmid DNA was linearized with a one cut restriction endonuclease (e.g., SacI), which cleaves 3' to the insert. Reaction conditions for the T7 in vitro reaction were: 40 mM Tris.HCl (pH 8), 30 mM MgCl$_2$, 10 mM β-mercaptoethanol, 50 μg/ml RNase/DNase-free bovine serum albumin (BSA), 500 μM each NTP, 100 ng of template, 0.3 U/μl of RNase inhibitor (Pharmacia) and 2 U/μl of T7 RNA polymerase (Pharmacia) in a final volume of 100 μl.

After incubation for 1 hour at 37° C., the DNA template was digested with 0.075 U/μl RNAse-free DNase I (Pharmacia) for 30 min. at 37° C. in order to eliminate template DNA. RNA was phenol extracted and ethanol precipitated.

For hypermutagenesis the reverse transcription reaction buffer was 50 mM Hepes (pH 7), 15 mM Mg Aspartate, 10 mM DTT, 55 mM K Acetate, 15 mM NaCl. The deoxynucleoside triphosphate (dNTP) concentrations were varied according to the permutations shown in the Table below:

| Type of permutation | dCTP | dTTP | dATP | dGTP |
|---|---|---|---|---|
| G-->A | 1-100 nM | 440 μM | 40 μM | 20 μM |
| U-->C | 10 μM | 44 μM | 1-100 nM | 200 μM |
| G-->A + U-->C | 1-100 nM | 440 μM | 1-100 nM | 200 μM |

Two picomoles of oligonucleotide (backward primer) (FIG. 3), complementary to positions just 3' to the target sequence to be hypermutated), were annealed to 0.5 pmol of the template RNA in 50 μl of the reaction by first heating to 65° C. for 1 min. followed by incubation at 37° C. for 1 min. after which 0.3 U/μl of RNase inhibitor and 15 pmol (6.25 units) of HIV-1 RTase (Boehringer) were added. The reaction was incubated at 37° C. for 3 hours.

In order to recover sufficient material for subsequent cloning, cDNA was amplified by PCR with the forward and backward primer pair (FIG. 3). Optimized PCR conditions were: 2.5 mM MgCl$_2$, 50 mM KCl, 10 mM Tris-HCl (pH 8.3), 200 μM of each dNTP, 5–20 μl of the reverse transcription reaction and 2.5 U of Taq DNA polymerase (Cetus) in a final volume of 100 μl. Annealing, extension and denaturation cycling parameters were: 37° C. (30s), 72° C. (30s) and 95° C. (30s) for 2 cycles and 55° C. (30s), 72° C. (30s) and 95° C. (30s) for 10 cycles. The low annealing temperature used in the first two cycles was designed to favor amplification of RNA sequences containing mutations in the PCR primer target sequence.

Once amplified, the DNA was cleaved by BamHI and SacI restriction endonucleases, which cut within the prime sequences (FIG. 3). The products were then ligated into the pTrc99A expression vector (Stratagene) at an equimolar ratio of insert to vector. After transformation of competent E. coil, cells were plated out onto standard LB (Lauria broth) plates supplemented with 100 μg/ml trimethoprim (TMP) and 100 μg/ml ampicillin (AMP).

To identify the nature of the hypermutated R67 genes, TMP resistant colonies were grown up singly, plasmid DNA extracted and the DNA was sequenced. The wild type R67 sequence is shown in FIG. 5.

EXAMPLE 3

In this example, RNA corresponding to the "palm" domain of nucleic acid polymerases (about 600 base pairs) is being subject to hypermutagenesis. The palm domain encodes the catalytic residues responsible for nucleic acid polymerization. The precise example here is the gene encoding the Klenow fragment of E. coli DNA polymerase I.

A plasmid "cassette" is made carrying the Klenow fragment gene under the control of a suitable promoter and including convenient and unique restriction sites around the region to be hypermutagenized. This cassette vector is obtained by conventional and existing mutagenesis procedures, such as those described by Sambrook et al. (supra).

The "palm" domain of the Klenow fragment is first amplified from the complete Klenow fragment using the standard PCR method; 2.5 mM MgCl$_2$, 50 mM Tris-HCl, pH 8.3, 50 mM KCl, 200 μM each dNTP, 100 mg plasmid DNA, 100 pmol of each primer in FIG. 3 and 2.5 U Taq polymerase (Cetus), in 15 cycles with the following cycling parameters: 30 sec. 92° C., 30 sec. 55° C. and 30 sec. 72° C. The amplification primers have T7 and T3 promoter sequences at their 5' extremities, i.e., forward primer, 5'     clamp—restriction     site—ATTAACCCTCACTAAAGGGA (SEQ. ID NO:6) (T3 promoter)—target specific sequence;

reverse primer

5'     clamp—restriction     site—AATTTAATACGACTCACTATAGGG (SEQ. ID NO:7)

(T7 promoter)—target specific sequence.

Following amplification RNA is made from either strand in a standard in vitro reaction. Reaction conditions for the T7 in vitro reaction were: 40 mM Tris.HCl (pH 8), 30 mM MgCl$_2$, 10 mM β-mercaptoethanol, 50 μg/ml RNase/DNase-free bovine serum albumin (BSA), 500 μM each NTP, 100 ng of template, 0.3 U/μl of RNase inhibitor (Pharmacia) and 2 U/μl of T7 RNA polymerase (Pharmacia) in a final volume of 100 μl.

After incubation for 1 hour at 37° C., the DNA template was digested with 0.075 U/μl RNAse-free DNase I (Pharmacia) for 30 min. at 37° C. in order to eliminate template DNA. RNA was phenol extracted and ethanol precipitated.

For hypermutagenesis the reverse transcription reaction buffer was 50 mM Hepes (pH 7), 15 mM Mg Aspartate, 10 mM DTT, 55 mM K Acetate, 15 mM NaCl. The deoxynucleoside triphosphate (dNTP) concentrations were varied according to the permutations shown in the Table below:

| Type of permutation | dCTP | dTTP | dATP | dGTP |
|---|---|---|---|---|
| G-->A | 1-100 nM | 440 μM | 40 μM | 20 μM |
| U-->C | 10 μM | 44 μM | 1-100 nM | 200 μM |
| G-->A + U-->C | 1-100 nM | 440 μM | 1-100 nM | 200 μM |

Two picomoles of oligonucleotide (backward primer) (FIG. 3), complementary to positions just 3' to the target sequence to be hypermutated), was annealed to 0.5 pmol of the template RNA in 50 μl of the reaction by first heating to 65° C. for 1 min. followed by incubation at 37° C. for 1 min. after which 0.3 U/μl of RNase inhibitor and 15 pmol (6.25 units) of HIV-1 RTase (Boehringer) were added. The reaction was incubated at 37° C. for 3 hours.

In order to recover sufficient material for subsequent cloning, cDNA is amplified by PCR with the forward and backward primer pair (FIG. 3). Optimized PCR conditions are 2.5 mM MgCl$_2$, 50 mM KCl, 10 mM Tris.HCl (pH 8.3), 200 μM of each dNTP, 5–20 μl of the reverse transcription reaction, and 2.5 U of Taq DNA polymerase (Cetus) in a final volume of 100 μl. Annealing, extension, and denaturation cycling parameters would be: 37° C. (30s), 72° C. (30s) and 95° C. (30s), for 2 cycles and 55° C. (30s), 72° C. (30s), and 95° C. (30s) for 10 cycles. The low annealing temperature used in the first two cycles is designed to favor amplification of RNA sequences containing mutations in the PCR primer target sequence.

Once amplified, the material is cleaved by the restriction sites introduced into the target sequence, which gave rise to the cassette vector. The products are ligated into the cassette vector. Genetic or phenotypic screening known by the man skilled in the art (Maniatis, Sambrook) is then employed.

EXAMPLE 4

Following Example 1 set forth above, the following reverse transcriptases of a retrovirus infecting mammalian cells and capable of inducing a mutation frequency comprised between $10^{-1}$ and $10^{-3}$ are utilized in lieu of HIV-1 reverse transcriptase: HIV-2 reverse transcriptase; feline immunodeficiency virus reverse transcriptase, an ungulate antivirus reverse transcriptase, simian immunodeficiency virus reverse transcriptase, avian myeloblastosis reverse transcriptase, moloney murine leukemia virus reverse transcriptase, the hepadnavirus reverse transcriptase and caulimovirus reverse transcriptase, and hypermutated variants.

EXAMPLE 5

Cell-lines containing a hypermutated gene carried by a vector or integrated in their genome also are prepared.

A feature of the hypermutagenesis reaction is that cDNA synthesis is not too efficient, being inversely proportional to the ratio of the concentrations of dCTP and dTTP, i.e. [dCTP]/[dTTP]. Given the power of PCR, it is usually possible to recover sufficient material to clone. However, it represents an impediment to exaggerating the [dCTP]/[dTTP] ratio, which would increase the degree of substitution of G by A. In order to alleviate these problems, this invention provides two ways of increasing the efficiency of cDNA synthesis during the hypermutagenesis reaction.

The first is to use multiple primers during the hypermutagenesis reaction instead of one (see FIG. 6). Conceptually it is very simple. A precise example is furnished in FIG. 7 where the use of the R67 encoded dihydrofolate reductase (DHFR) gene as target sequence is exemplified. Of course, the hypermutagenesis reaction can be utilized with any RNA sequence. More particularly, instead of adding a single oligodesoxyribonucleotide (or primer) to the RNA, three reactions are set up with only one primer in each (primers 1, 2 and 3 in FIGS. 6 and 7). With very biased [dCTP]/[dTTP] ratios, short segments, less than the full length complementary sequence, can be produced.

After the hypermutagenesis reactions, a sample from each of the three reactions is taken and mixed together in PCR buffer along with the outer pair of primers 3 and 4 (FIGS. 6 and 7). The cDNA fragments made in the hypermutagenesis reaction serve as the initial templates for PCR using the left primer 4. PCR recombination (Meyerhans et al. 1991) assures assembly of the full length, yet hypermutated, R67 sequences. Once PCR material is obtained, conventional molecular biology is employed.

While this example mentions a biased [dCTP]/[dTTP] ratio, it will be understood that this technique can equally be performed with a biased [dATP]/[dGTP] ratio as previously mentioned. In the present example, three primers were used to hypermutate R67 RNA. Three have been used efficiently. However, nothing prevents the use of 2, 4, or more primers. Indeed, the longer the target RNA, then the more the number of primers necessary.

Thus, this technique makes it possible to recover hypermutated RNA more easily and with greater efficiency than before. This embodiment of the invention resides in the recognition that multiple primers allow recovery of short cDNA fragments made during the reaction. It relies on the recombinatorial power of PCR to assemble DNA fragments. See Meyerhans, A., Vartanian, J. P. & Wain-Hobson, S. (1992) Nucl. Acids Res. 20, 521–523 and Stemmer, W. P. C. (1994) Nature 370, 389–391.

A second modification of the invention involves a conceptually very different physical means to hypermutagenize RNA. This modification is shown in FIG. 8 and involves hypermutagenesis by dialysis. This embodiment stems from the realization that during cDNA synthesis, under biased deoxyribonucleoside triphosphate (dNTP) concentrations, the dCTP concentration, for example, is not constant but is being depleted resulting in poor cDNA synthesis. This poses the problem as to how a given bias can be maintained. Following is a simple solution, which allows cDNA synthesis under highly biased but constant dNTP ratios. Once again, the R67 DHFR gene RNA is used as an example, but of course any other RNA sequence can be used.

The components are those previously described, i.e. R67 RNA, the outer primer 3 (FIG. 7), reaction buffer, HIV-1 reverse transcriptase, but no dNTPs. The composition of this mix was: 50 mM Hepes (pH 7), 15 mM Mg Aspartate, 10 mM DTT, 55 mM K Acetate, 15 mM NaCl. Two picomoles of oligonucleotide (primer 3, FIG. 6), complementary to positions just 3' to the target sequence to be hypermutated, were annealed to 0.5 pmol of the template RNA in 50 μl of the reaction by first heating to 65° C. for 1 min. followed by incubation at 37° C. for 1 min. after which 0.3 U/μl of RNase inhibitor and 15 pmol (6.25 units) of HIV-1 RTase (Boehringer) were added. Instead of carrying out the reaction in a closed plastic tube, the 50 μl (typically, but not exclusively) reaction volume is placed upon a 0.025 μm nitrocellulose filter as in FIG. 8.

In the meantime, approximately 10–15 ml of reaction buffer and dNTPs are placed in a Petri dish and prewarmed at 37° C. without shaking for approximately 20–30 minutes. The composition of this mix was: 50 mM Hepes (pH 7), 15 mM Mg Aspartate, 10 mM DTT, 55 mM K Acetate, 15 mM NaCl. The deoxynucleoside triphosphate (dNTP) concentrations are varied. Typical permutations are shown below:

| Type of of permutation | dCTP | dTTP | dATP | dGTP |
|---|---|---|---|---|
| G-->A | 3-100 nM | 440 μM | 40 μM | 20 μM |
| U-->C | 10 μM | 44 μM | 3-100 nM | 200 μM |
| G-->A + U-->C | 3-100 nM | 440 μM | 3-100 nM | 200 μM |

The reaction volume was placed on the cellulose-based filter and was left at 37° C. for 3 hours without shaking. The dNTPs dialyze into the 50 μl reaction volume in a matter of minutes thereby starting the hypermutagenesis reaction. However, given the huge excess of dNTPs in the volume under the filter (some 200 fold), the dNTP ratios hardly change throughout the reaction. After hypermutagenesis, a sample was amplified by PCR using oligos 3 and 4 (FIG. 7) by standard techniques.

While the invention has been described in terms of various preferred embodiments, the skilled artisan will appreciate that various modifications, substitutions, omissions, and changes may be made without departing from the scope thereof. Accordingly, it is intended that the scope of the present invention be limited by the scope of the following claims, including equivalents thereof.

What is claimed is:

1. A method for introducing hypermutations into a target nucleotide sequence, wherein said method comprises:
   reverse transcribing an RNA sequence in a reaction mixture comprising a reverse transcriptase, dATP, dTTP, dCTP, and dGTP with varying biased concentrations of said deoxynucleoside triphosphates, and an oligonucleotide primer that is partially complementary to the 3' end of said RNA sequence, to thereby produce a hypermutated DNA sequence.

2. The method according to claim 1, wherein said RNA sequence has been isolated from total RNA.

3. The method according to claim 2, wherein said RNA sequence is mRNA isolated from said total RNA.

4. The method according to claim 3, which further comprises separating said hypermutated DNA sequence from said reaction mixture.

5. The method according to claim 1, wherein said RNA sequence is generated in vitro from a plasmid or phage vector.

6. The method of claim 5, wherein said plasmid vector is selected from the group consisting of pGEM-3, pGEM-4, pGEM-3Z, pGEM-3ZF, Bluescript M13$^+$, Bluescript M13$^-$, pBluescript KS$^+$, and pBluescript SK$^+$.

7. The method according to claim 5, wherein said vector is pBluescript SK$^+$ or pBluescript KS$^+$.

8. The method according to claim 1, wherein said reverse transcriptase is selected from the group consisting of human immunodeficiency virus-1 reverse transcriptase, human immunodeficiency virus-2 reverse transcriptase, feline immunodeficiency virus reverse transcriptase, simian immunodeficiency virus reverse transcriptase, hepadnavirus virus reverse transcriptase, and ungulate lentivirus reverse transcriptases, and hypermutated variations of these reverse transcriptases having reverse transcriptase activity.

9. The method according to claim 1, wherein said reverse transcriptase is present in a large molar excess of RNA sequence.

10. The method according to claim 1, wherein the reverse transcriptase:RNA sequence ratio is 30:1 or 50:1.

11. The method according to claim 1, wherein said RNA sequence is reverse transcribed at 37° C. for 3 hours in said reaction mixture.

12. The method according to claim 1, wherein said deoxynucleoside triphosphates are present in the reaction mixture at biased pyrimidine concentrations between about 1 nM to 100 nM dCTP, and about 440 $\mu$M dTTP, about 20 $\mu$M dGTP, and about 40 $\mu$M dATP thereby producing G to A hypermutations in said hypermutated DNA sequence.

13. The method according to claim 1, wherein said deoxynucleoside triphosphates are present in the reaction mixture at biased purine concentrations, of about 1 nM to about to 100 nM dCTP, about 1 to 100 nM, ATP, about 440 $\mu$M dTTP, and about 200 $\mu$M dGTP thereby producing U to C hypermutations in said hypermutations DNA sequence.

14. The method according to claim 1, wherein said deoxynucleoside triphosphates are present in concentrations to produce G to A and U to C hypermutations.

15. The method according to claim 1, wherein said oligonucleotide primer has about 12 to 50 nucleotides complementary to the 3' end of said RNA sequence.

16. A method for introducing hypermutations into a target nucleotide sequence, wherein said method comprises:
   (a) providing a vector containing a nucleotide sequence in double-stranded form;
   (b) transcribing the nucleotide sequence into an RNA sequence in vitro;
   reverse transcribing said RNA sequence in a reaction mixture comprising a reverse transcriptase, dATP, dTTP. dCTP, and dGTP with varying biased concentrations of said deoxynucleoside triphosphates, and an oligonucleotide primer that is partially complementary to the 3' end of said RNA sequence, to thereby produce a hypermutated DNA sequence.

17. The method according to claim 16, wherein both strands of the double-stranded nucleotide sequence are capable of being transcribed into the RNA sequence.

18. The method according to claim 1 or claim 16, further comprising amplifying said hypermutated DNA sequence by PCR.

19. The process according to claim 1 or claim 16, further comprising:
   ligating said hypermutated DNA sequence into a vector; and
   transforming a cell host with said vector containing said hypermutated DNA sequence.

20. A process for introducing hypermutations into a target nucleotide sequence, wherein said process comprises:
   (a) providing a vector containing a nucleotide sequence and a T7 or a T3 promoter sequence;
   (b) transcribing the nucleotide sequence into an RNA sequence by using T7 or T3 RNA polymerase;
   (c) reverse transcribing said RNA sequence in a reaction mixture comprising a reverse transcriptase, dATP, dTTP, dCTP, and dGTP with varying biased concentrations of said deoxynucleoside triphosphates, and an oligonucleotide primer that is partially complementary to the 3' end of said target RNA sequence, to thereby produce a hypermutated DNA sequence.

21. The method according to claim 20, further comprising amplifying said hypermutated DNA sequence by PCR.

22. The method according to any one of claims 1, 16, or 20, further comprising cloning said hypermutated DNA sequence into vector.

23. A method of producing a hypermutated protein comprising:

(a) providing an expression vector containing a hypermutated DNA sequence produced by the method of any one of claims 1, 16, or 20, wherein the hypermutated DNA sequence codes for a protein and (b) expressing the hypermutated DNA sequence to produce a hypermutated protein.

24. A method for introducing hypermutations into a target nucleotide sequence, wherein the method comprises:

(A) providing a reaction mixture consisting essentially of
(1) a RNA template to be hypermutated;
(2) reverse transcriptase for reverse transcribing the RNA template to form cDNA, wherein the RNA template and reverse transcriptase are in a molar ratio of about 30:1 to about 50:1;
(3) an oligonucleotide primer for initiating cDNA synthesis along the template, wherein the oligonucleotide primer is present in a molar excess relative to the RNA template; and
(4) a mixture of deoxynucleoside triphosphates comprising dATP, dTTP, dGTP, dCTP, wherein molar concentrations of said deoxynucleoside triphosphates are biased such that
   (a) the concentration of dCTP is low relative to the concentration of dTTP; or
   (b) the concentration of dATP is low relative to the concentration of dGTP; or
   (c) the sum of the concentrations of dCTP and dATP is low relative to the sum of the concentrations of dTTP and dGTP; and (B) reverse transcribing said RNA template to form a hypermutated nucleotide sequence having G→A mutations, U→C mutations, or mixed G→A and U→C mutations in which about 2% to about 99% of the nucleotides in the RNA template are mutated.

25. The method as claimed in claim 24, wherein the reverse transcriptase is HIV-1 reverse transcriptase.

26. The method as claimed in claim 24, wherein the reverse transcriptase is HIV-2 reverse transcriptase.

27. The method as claimed in claim 24, wherein the method further comprises: (a) recovering the hypermutated nucleotide sequence; (b) transcribing the hypermutated nucleotide sequence into a RNA template; and (c) repeating the method of claim 24, wherein a different oligonucleotide primer is employed.

28. The method as claimed in claim 24, wherein deoxynucleoside triphosphates are in a first reaction zone that is separated by a dialysis membrane from a second reaction zone containing the RNA template, reverse transcriptase, and oligonucleotide primer; and
wherein the deoxynucleoside triphosphates enter the second reaction zone by dialysis through said membrane to thereby provide a substantially uniform concentration of deoxynucleoside triphosphates to the second reaction zone for cDNA synthesis.

29. The method as claimed in claim 24, wherein the molar ratio of dCTP to dTTP is about $10^{-2}$ to about $2\times10^{-5}$.

30. The method as claimed in claim 24, wherein the molar ratio of dATP to dGTP is about $10^{-2}$ to about $2\times10^{-5}$.

31. The method as claimed in claim 24, wherein dATP and dGTP are at concentrations that saturate reverse transcriptase.

32. The method of claim 1, wherein said RNA sequence is generated from a DNA sequence.

33. The method of claim 32, wherein the DNA sequence is cDNA sequence.

34. The method of either claim 1, 16, 21, or 24 wherein the nucleotide sequence is a DNA sequence.

35. The method of claim 34, wherein the DNA sequence is cDNA.

36. The method of claim 24, wherein the RNA template is generated from a DNA sequence.

37. The method of claim 36, wherein the DNA sequence is cDNA.

38. The method of claim 22, wherein the vector is an expression vector.

39. The method according to any one of claims 1, 16, or 20, wherein said oligonucleotide primer has greater than 10 nucleotides complementary to the 3' end of said target RNA sequence.

40. The method of claim 24, wherein less than 5% of the nucleotides in the RNA template are mutated in the hypermutated nucleotide sequence.

41. The method of claim 24, wherein about 2% to about 20% of the nucleotides in the RNA template are mutated in the hypermutated nucleotide sequence.

42. The method of claim 24, wherein about 5% to about 80% of the nucleotides in the RNA template are mutated in the hypermutated nucleotide sequence.

43. The method of claim 24, wherein about 5% to about 50% of the nucleotides in the RNA template are mutated in the hypermutated nucleotide sequence.

44. The method of claim 24, wherein about 5% to about 95% of the nucleotides in the RNA template are mutated in the hypermutated nucleotide sequence.

45. A method of producing a hypermutated protein comprising:

(a) providing an expression vector containing a hypermutated nucleotide sequence produced by the method of claim 24, wherein the hypermutated DNA sequence codes for a protein and (b) expressing the hypermutated nucleotide sequence to produce a hypermutated protein.

* * * * *

UNITED STATES PATENT AND TRADEMARK OFFICE
CERTIFICATE OF CORRECTION

PATENT NO. : 5,843,730
DATED : December 1, 1998
INVENTOR(S) : WAIN-HOBSON et al.

It is certified that error appears in the above-identified patent and that said Letters Patent is hereby corrected as shown below:

On the Title Page, Item [75], in the Inventors, line 1, "Montiguy" should read --Montigny--; and line 2, "Bretonneloc" should read --Bretonneux--.

In Claim 13, col. 49, line 67, before "100 nM dCTP", delete "about to"; and "100 nM, ATP," should read --100 nM ATP,--.

In Claim 13, col. 50, line 16, "hypermutations DNA" should read --hypermutated DNA--.

In Claim 16, col. 50, line 28, before "reverse", insert --(c)--.

In Claim 20, col. 50, line 65, after "into", insert --a--.

In Claim 23, col. 51, line 4, after "protein", insert --;--.

In Claim 45, col. 52, line 48, after "protein", insert --;--.

Signed and Sealed this

Twentieth Day of July, 1999

Attest:

*Attesting Officer*

Q. TODD DICKINSON

*Acting Commissioner of Patents and Trademarks*